(12) United States Patent
Swift et al.

(10) Patent No.: US 7,256,251 B2
(45) Date of Patent: Aug. 14, 2007

(54) METHODS OF SYNTHESIS OF POLYMERS AND COPOLYMERS FROM NATURAL PRODUCTS

(75) Inventors: Graham Swift, Chapel Hill, NC (US); David G. Westmoreland, Hillsborough, NC (US); Julious L. Willett, Morton, IL (US); Randal Lee Shogren, Chillicothe, IL (US); Kenneth Michael Doll, Peoria, IL (US)

(73) Assignee: Folia Inc., Birmingham, AL (US)

( * ) Notice: Subject to any disclaimer, the term of this patent is extended or adjusted under 35 U.S.C. 154(b) by 402 days.

(21) Appl. No.: 11/059,678

(22) Filed: Feb. 17, 2005

(65) Prior Publication Data

US 2005/0192426 A1 Sep. 1, 2005

Related U.S. Application Data

(63) Continuation-in-part of application No. 10/834,908, filed on Apr. 30, 2004, now abandoned, which is a continuation-in-part of application No. 10/698,375, filed on Nov. 3, 2003, now Pat. No. 7,074,881, and a continuation-in-part of application No. 10/698,411, filed on Nov. 3, 2003, now Pat. No. 6,903,181, and a continuation-in-part of application No. 10/698,398, filed on Nov. 3, 2003, now Pat. No. 6,887,971, said application No. 10/698,375 is a continuation-in-part of application No. 10/307,349, filed on Dec. 2, 2002, now Pat. No. 6,686,440, and a continuation-in-part of application No. 10/307,387, filed on Dec. 2, 2002, now Pat. No. 6,686,441, said application No. 10/698,411 is a continuation-in-part of application No. 10/307,349, and a continuation-in-part of application No. 10/307,387, said application No. 10/698,398 is a continuation-in-part of application No. 10/307,349, and a continuation-in-part of application No. 10/307,387, said application No. 10/307,349 is a continuation of application No. 09/776,897, filed on Feb. 6, 2001, now Pat. No. 6,495,658, said application No. 10/307,387 is a continuation-in-part of application No. 09/776,897.

(51) Int. Cl.
*C08G 65/34* (2006.01)
*C08G 63/66* (2006.01)

(52) U.S. Cl. .................. 528/361; 528/425; 528/486; 528/503; 525/419

(58) Field of Classification Search .............. 528/361, 528/425, 486, 503; 525/419
See application file for complete search history.

(56) References Cited

U.S. PATENT DOCUMENTS

| | | | |
|---|---|---|---|
| 6,495,658 B2 * | 12/2002 | Sikes et al. | 528/363 |
| 6,686,440 B2 * | 2/2004 | Swift | 528/363 |
| 6,686,441 B2 * | 2/2004 | Swift et al. | 528/363 |
| 6,887,971 B2 * | 5/2005 | Swift et al. | 528/328 |
| 6,903,181 B2 * | 6/2005 | Swift et al. | 528/328 |

* cited by examiner

*Primary Examiner*—Duc Truong
(74) *Attorney, Agent, or Firm*—Stamatios Mylonakis

(57) ABSTRACT

Described are polymers and copolymers containing sorbitol, citric acid, starch, aspartic acid, succinic anhydride, adipic acid mixtures thereof, methods of their synthesis and their uses.

33 Claims, 12 Drawing Sheets

METHODS OF SYNTHESIS OF POLYMERS AND COPOLYMERS FROM NATURAL PRODUCTS

This application is a CIP of application Ser. No. 10/834,908, filed Apr. 30, 2004 ABN; and said Ser. No. 10/834,908 is a CIP of Ser. No. 10/698,375, filed Nov. 3, 2003 now U.S. Pat. No. 7,074,881; and is a CIP of Ser. No. 10/698,411, filed Nov. 3, 2003; and is a CIP of Ser. No. 10/698,398 filed Nov. 3, 2003 U.S. Pat. Nos. 6,903,181 and 6,887,971; and said Ser. No. 10/698,375 is a CIP of Ser. No. 10/307,349, filed Dec. 2, 2002 now U.S. Pat. No. 6,686,440; and said Ser. No. 10/698,375 is a CIP of Ser. No. 10/307,387, filed Dec. 2, 2002 now U.S. Pat. No. 6,686,441; and said Ser. No. 10/698,411 is a CIP of Ser. No. 10/307,349, filed Dec. 2, 2002 now U.S. Pat. No. 6,686,440; and said Ser. No. 10/698,411 is a CIP of Ser. No. 10/307,387, filed Dec. 2, 2002 now U.S. Pat. No. 6,686,441; and said Ser. No. 10/698,398 is a CIP of Ser. No. 10/307,349, filed Dec. 2, 2002 now U.S. Pat. No. 6,686,440; and said Ser. No. 10/698,398 is a CIP of Ser. No. 10/307,387, filed Dec. 2, 2002 now U.S. Pat. No. 6,686,441; and said Ser. No. 10/307,349 is a Continuation of Ser. No. 09/776,897, filed Feb. 6, 2001, now U.S. Pat. No. 6,495,658; and said Ser. No. 10/307,387 is a CIP of Ser. No. 09/776,897, filed Feb. 6, 2001, now U.S. Pat. No. 6,495,658, each of which is incorporated herein by reference in its entirety.

BACKGROUND OF THE INVENTION

1. Field of the Invention

The present invention relates to a process for the preparation of polymers and copolymers of sorbitol-citric acid, sorbitol-citric acid-starch, sorbitol-aspartic acid, sorbitol-aspartic acid-starch, aspartic acid-succinic anhydride, aspartic acid-adipic acid, aspartic acid-adipic acid-succinic anhydride, combinations thereof and their use as thickeners, detergents, absorbents, or water transfer seed coatings. The polymers of the present invention are also useful as biodegradable polymers.

2. Discussion of the Related Art

L-Aspartic acid has been produced commercially since the 1980's via immobilized enzyme methods. The L-aspartic acid so produced mainly has been used as a component of the synthetic sweetener, N-aspartylphenylalaninemethyl ester (ASPARTAME®).

In a typical production pathway, a solution of ammonium maleate is converted to fumarate via action of an immobilized enzyme, maleate isomerase, by continuous flow over an immobilized enzyme bed. Next, the solution of ammonium fumarate is treated with ammonia also by continuous flow of the solution over a bed of the immobilized enzyme, aspartase. A relatively concentrated solution of ammonium asparate is produced, which then is treated with an acid, for example nitric acid, to precipitate L-aspartic acid. After drying, the resultant product of the process is powdered or crystalline L-aspartic acid. Prior art that exemplifies this production pathway includes U.S. Pat. No. 4,560,653 to Sherwin and Blouin (1985), U.S. Pat. No. 5,541 to Sakano et al. (1996), and U.S. Pat. No. 5,741,681 to Kato et al. (1998).

In addition, non-enzymatic, chemical routes to D,L aspartic acid via treatment of maleic acid, fumaric acid, or their mixtures with ammonia at elevated temperature have been known for over 150 years (see Harada, K., *Polycondensation of thermal precursors of aspartic acid. Journal of Organic Chemistry* 24, 1662-1666 (1959); also, U.S. Pat. No. 5,872,285 to Mazo et al. (1999)). Although the non-enzymatic routines are significantly less quantitative than the enzymatic syntheses of aspartic acid, possibilities of continuous processes and recycling of reactants and by-products via chemical routes are envisioned.

Polymerization and copolymerization of L-aspartic acid alone or with other comonomers is known. As reviewed in U.S. Pat. No. 5,981,691 to Sikes (1999), synthetic work with polyamino acids, beginning with the homopolymer of L-aspartic acid, dates to the mid 1800's and has continued to the present. Interest in polyaspartates and related molecules increased in the mid 1980's as awareness of the commercial potential of these molecules grew. Particular attention has been paid to biodegradable and environmentally compatible polyaspartates for commodity uses such as detergent additives and superabsorbent materials in disposable diapers, although numerous other uses have been contemplated, ranging from water-treatment additives for control of scale and corrosion to anti-tartar agents in toothpastes.

There have been some teachings of producing copolymers of succinimide and L-aspartic acid or aspartate via thermal polymerization of maleic acid plus ammonia or ammonia compounds. For example, U.S. Pat. No. 5,548,036 to Kroner et al. (1996) taught that polymerization at less than 140° C. resulted in aspartic acid residue-containing polysuccinimides. However, the reason that some aspartic acid residues persisted in the product polymers was that the temperatures of polymerization were too low to drive the reaction to completion, leading to inefficient processes.

JP 8277329 (1996) to Tomida exemplified the thermal polymerization of potassium asparate in the presence of 5 mole % and 30 mole % phosphoric acid. The purpose of the phosphoric acid was stated to serve as a catalyst so that molecules of higher molecular weight might be produced. However, the products of the reaction were of a lower molecular weight than were produced in the absence of the phosphoric acid, indicating that there was no catalytic effect. There was no mention of producing copolymers of aspartate and succinimide; rather, there was mention of producing only homopolymers of polyaspartate. In fact, addition of phosphoric acid in this fashion to form a slurry or intimate mixture with the powder of potassium aspartate, is actually counterproductive to formation of copolymers containing succinimide and aspartic acid residue units, or to formation of the condensation amide bonds of the polymers in general. That is, although the phosphoric acid may act to generate some fraction of residues as aspartic acid, it also results in the occurrence of substantial amounts of phosphate anion in the slurry of mixture. Upon drying to form the salt of the intimate mixture, such anions bind ionically with the positively charged amine groups of aspartic acid and aspartate residues, blocking them from the polymerization reaction, thus resulting in polymers of lower molecular weight in lower yield.

Earlier, U.S. Pat. No. 5,371,180 to Groth et al. (1994) had demonstrated production of copolymers of succinimide and aspartate by thermal treatment of maleic acid plus ammonium compounds in the presence of alkaline carbonates. The invention involved an alkaline, ring-opening environment of polymerization such that some of the polymeric succinimide residues would be converted to the ring-opened, aspartate form. For this reason, only alkaline carbonates were taught and there was no mention of cations functioning themselves in any way to prevent imide formation.

More recently, U.S. Pat. No. 5,936,121 to Gelosa et al. (1999) taught formation of oligomers (Mw<1000) of aspartate having chain-terminating residues of unsaturated dicarboxylic compounds such as maleic and acrylic acids. These aspartic-rich compounds were formed via thermal condensation of mixtures of sodium salts of maleic acid plus ammonium/sodium maleic salts that were dried from solutions of ammonium maleate to which NaOH had been added. They were producing compounds to sequester alkaline-earth metals. In addition, the compounds were shown to be non-toxic and biodegradable by virtue of their aspartic acid composition. Moreover, the compounds retained their biodegradability by virtue of their very low Mw, notwithstanding the presence of the chain-terminating residues, which when polymerized with themselves to sizes about the oligomeric size, resulted in non-degradable polymers.

A number of reports and patents in the area of polyaspartics (i.e., poly(aspartic acid) or polyaspartate), polysuccinimides, and their derivatives have appeared more recently. Notable among these, for example, there have been disclosures of novel superabsorbents (U.S. Pat. No. 5,955, 549 to Chang and Swift, 1999; U.S. Pat. No. 6,027,804 to Chou et al., 2000), dye-leveling agents for textiles (U.S. Pat. No. 5,902,357 to Riegels et al., 1999), and solvent-free synthesis of sulfhydryl-containing corrosion and scale inhibitors (EP 0 980 883 to Oda, 2000). There also has been teaching of dye-transfer inhibitors prepared by nucleophilic addition of amino compounds to polysuccinimide suspended in water (U.S. Pat. No. 5,639,832 to Kroner et al., 1997), which reactions are inefficient due to the marked insolubility of polysuccinimide in water.

U.S. Pat. No. 5,981,691 purportedly introduced the concept of mixed amide-imide, water-soluble copolymers of aspartate and succinimide for a variety of uses. The concept therein was that a monocationic salt of aspartate when formed into a dry mixture with aspartic acid could be thermally polymerized to produce the water-soluble copoly (aspartate, succinimide). The theory was that the aspartic acid comonomer when polymerized led to succinimide residues in the product polymer and the monosodium aspartate comonomer led to aspartate residues in the product polymer. It was not recognized that merely providing the comonomers was not sufficient to obtain true copolymers and that certain other conditions were necessary to avoid obtaining primarily mixtures of polyaspartate and polysuccinimide copolymers. In U.S. Pat. No. 5,981,691, the comonomeric mixtures were formed from an aqueous slurry of aspartic acid, adjusted to specific values of pH, followed by drying. There was no teaching of use of solutions of ammonium aspartate or any other decomposable cation plus NaOH, or other forms of sodium or other cations, for generation of comonomeric compositions of aspartic acid and salts of aspartate. Thus, although some of the U.S. Pat. No. 5,981,691 examples obtain products containing some copolymer in mixture with other products, particularly homopolymers, as discussed in the Summary of the Invention below, the theory that true copolymers could be obtained merely by providing the comonomers in the manner taught in U.S. Pat. No. 5,981,691 was not fully realized. Further, there have been no successful disclosures of end capping polymerizations of succinic anhydride-aspartic acid in the presence of sorbitol, starch or adipic acid.

SUMMARY OF THE INVENTION

The present invention includes copolymers of sorbitol, such as copolymers of sorbitol with citric acid, in the presence or absence of starch, copolymers of sorbitol with L-aspartic acid, in the presence or absence of starch, copolymers of sorbitol with L-aspartic acid and succinic anhydride and methods for their production. The copolymers of the present invention are polymerized by thermal polymerization, and particularly, by melt processing, such as in an extruder, to obtain useful products as thickeners, detergents, absorbents, water transfer seed coatings and biodegradable materials. A further aspect of the present invention allows the introduction of specific end functionality into the polymer.

DESCRIPTION OF THE PREFERRED EMBODIMENTS

A method has now been discovered providing copolymers of D-sorbitol with citric acid, L-aspartic acid, succinic anhydride and starch and mixtures thereof. Polymers or copolymers comprised of materials of natural resources, such as L-aspartic acid, succinimide, citric acid, sorbitol, and starch find uses as thickeners, detergents, absorbents, water transfer seed coatings and biodegradable materials. Additionally, the bio-based source of these reactants allows the potential for use in the food, cosmetics, and personal care industries. One use of amino acid cross linking is in the textile industry, where desirable properties in cotton fabric can be obtained using aspartic acid or glutamic acid in place of more traditional cross linking agents such as dimethyloldihydroxyethylene urea.

D-sorbitol is a reduced form of glucose which is common from natural resources. It is used in large volumes and accounted for 48% of the 1.3 billion dollar polyol market in 2001. Current prices of D-sorbitol are as low as $0.25 per lb. Polyesters of D-sorbitol and other dicarboxylates including adipic acid, divinyladipate, and divinylsebacate, (in some cases, 1,8-octanediol is also added), have been previously synthesized using a lipase enzyme catalyst, and a graft of D-sorbitol to L-phenylalanine has been synthesized using *Bacillus subtilis* protease in dimethylformamide. Work has also been performed on the use of D-sorbitol esters of fatty acids as drying oils, in systems which also show the dehydration of the D-sorbitol to the expected anhydrosorbitol ester. Despite all of this work, copolymer of L-aspartic acid and D-sorbitol have not been reported.

Early work on polyesters of citric acid yielded resins and adhesives. Recently, polymers of citric acid or copolymers with polyhydroxy compounds and amino compounds have been synthesized and show promise in the detergent industry. However, a solvent free synthesis, subject of the present invention, presents an advantage over the aqueous or solvent systems. Citric acid or salts of citric acid are known to react with alcohols or polyols to form esters. Copolyesters of citric acid and 1,2,6-hexane triol have also been considered as possible candidates for drug delivery. The present invention teaches novel copolymers of sorbitol and methods for producing the copolymers of sorbitol.

I. Citric Acid-D-Sorbitol Copolymers

Figure 1:
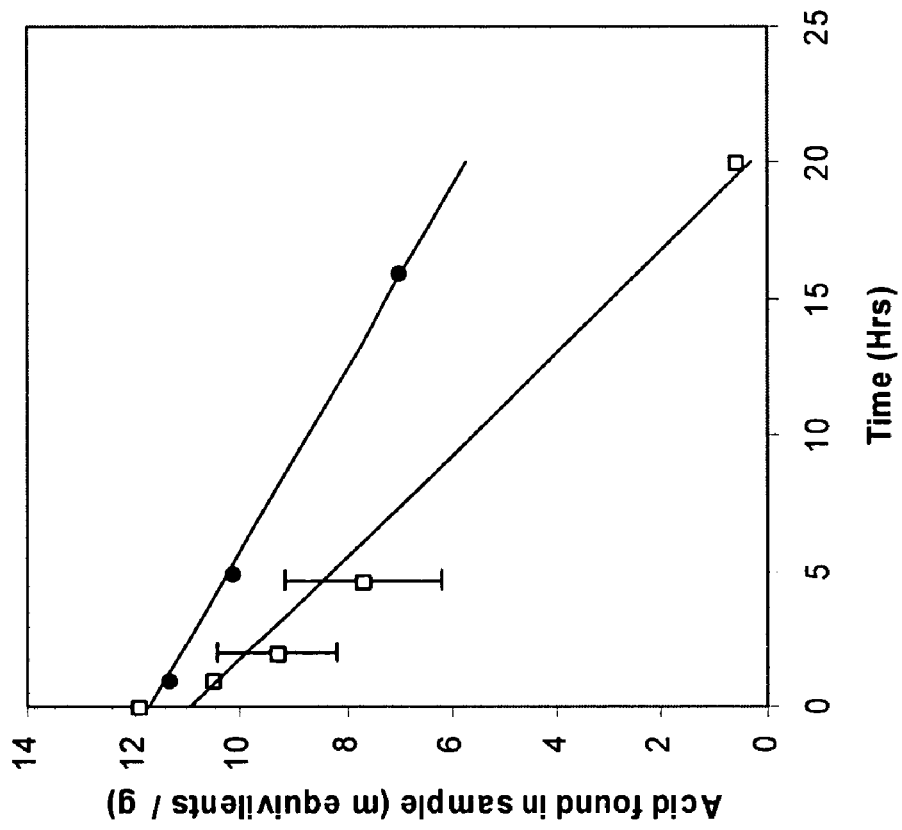
FIG. 1. The amount of acid in the sample found by titration analysis of samples taken during the polymerization of a 3/1 molar ratio citric acid/D-sorbitol. The reactions were run at 150° C. (□) and 110° C. (●). (The error bars were determined from analysis of multiple reactions).

In one embodiment in accordance with the present invention copolymers of citric acid with D-sorbitol were synthesized using a solvent free synthesis. In accordance with this embodiment D-sorbitol is first melted, then the citric acid is stirred into the melt. The mixture is then placed in a vacuum oven at an oven temperature in the range of 100° C. to 250° C. In two experiments in accordance with this embodiment the temperature of the oven was increased to 110° C. or 150° C. The condensation reaction was followed by sampling the system and performing a titration analysis. A plot of the results (FIG. 1) shows that the reaction is significantly faster at the higher temperature. Preferably, the molar ratio of citric acid to D-sorbitol is in the range of from 1:1 to 10:1; more preferably from 1:1 to 6:1; even more preferably from 2:1 to 4:1 and most preferably from 2:1 to 3:1. Surprisingly, despite the small amount of carbohydrate used in the synthesis of the above compositions, the insoluble materials displayed measurable water absorption properties (Table 1), demonstrating the potential use as a bio-based absorbent. Although Applicants do not wish to be bound to any particular theory, they believe that the reaction in accordance with this embodiment follows the Scheme 1 below. In accordance with Scheme 1 the polymerization reaction of citric acid and D-sorbitol proceeds through an anhydride intermediate. Citric acid can then undergo further condensation and the resulting cross-linking can give an insoluble material under certain conditions. The terminal hydroxy group on the sorbitol is shown to react for clarity. Reaction at the other hydroxy groups may also occur.

Scheme 1

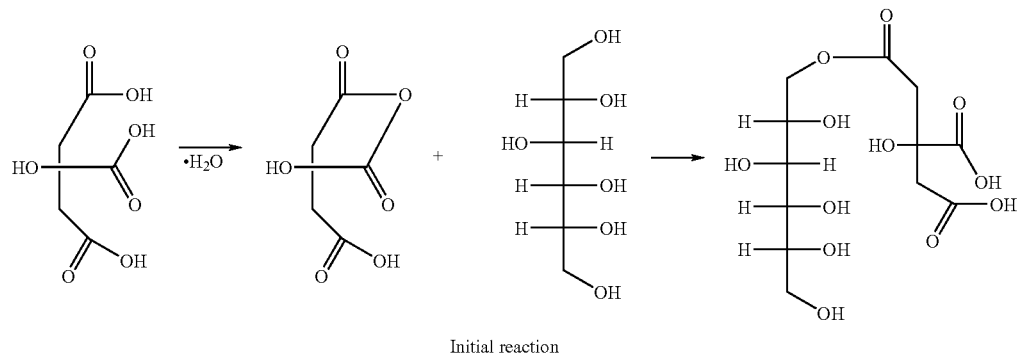

Initial reaction

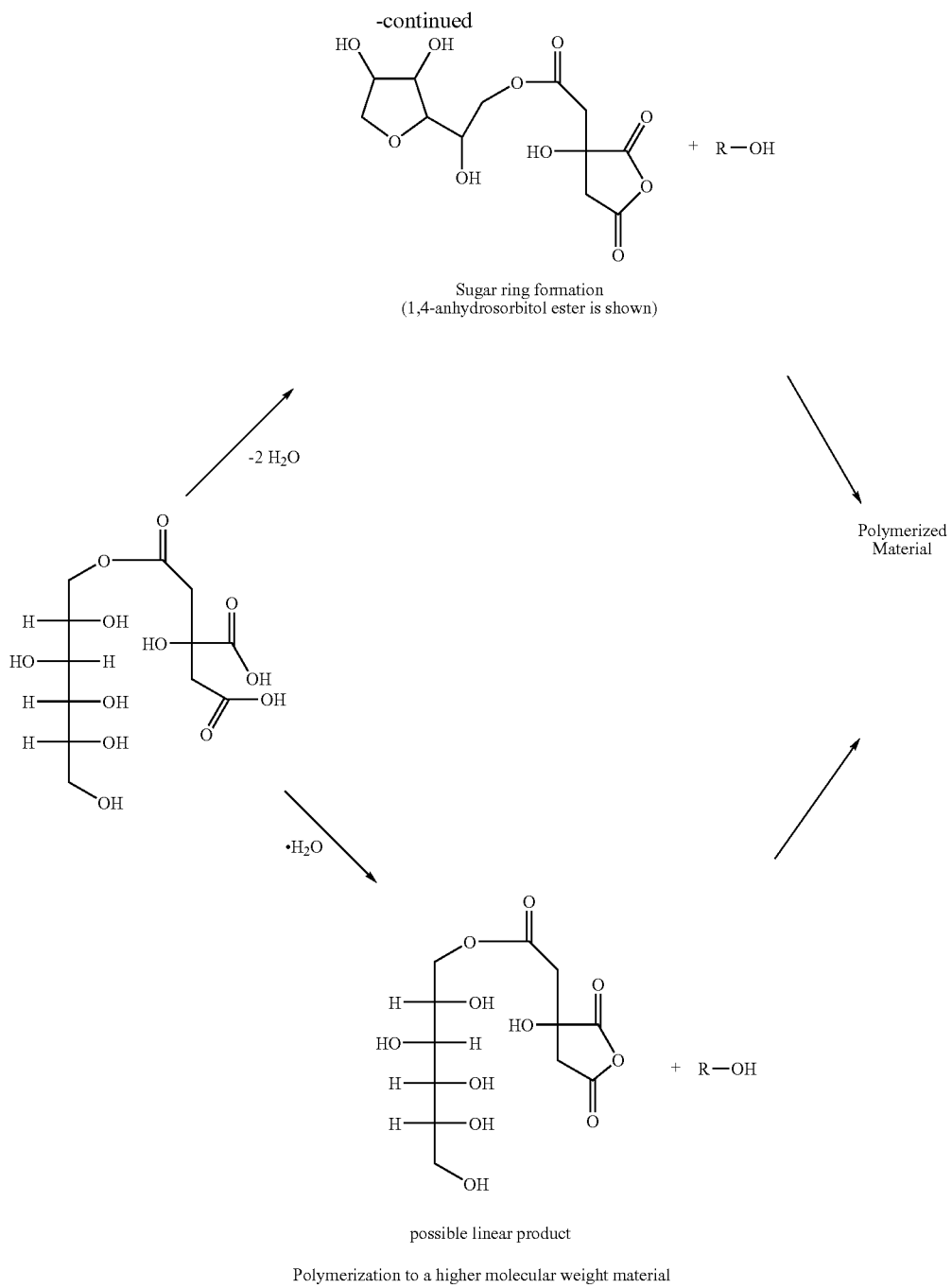

Polymerization to a higher molecular weight material

Sodium Citrate-D-Sorbitol Copolymers

In another embodiment of the present invention a soluble copolymer suitable for use as detergent builder was synthesized. The purpose of the builder in a detergent is to increase performance by sequestering of ions. Because of the ability of citric acid to bind ions, a soluble citrate-D-sorbitol copolymer is a potential detergent builder. A molecular structure containing at least 10 glucose units is also considered an advantage. In order to synthesize a material which would remain soluble, we performed similar polymerizations using the various sodium salts of citric acid. Because the reaction pathway for formation of citric esters may be through citric anhydrides, it is believed that the presence of sodium salt slows the crosslinking of the material enabling the synthesis of a soluble material with a desired large carboxylate content and a fairly low number of sorbitol units.

In addition to sodium, suitable counter ions to form a salt with the citric acid in accordance with the present invention include, but are not limited to cations of Group Ia, IIa, IIIa, IVa, Va, VIa, VIIa, VIIIa, Ib, IIb, and IIIb and combinations thereof, of the periodic Table of Elements. Preferred are cations of Group Ia, such as: $Li^+$, $Na^+$, $K^+$, $Rb^+$, and $Cs^+$ and combinations thereof, cations of Group Ia, such as $Mg^{++}$, $Ca^{++}$, $Sr^{++}$ and $Ba^{++}$ and combinations thereof. Further, H2-Citrate, H-Citrate or a fully neutralized Citrate are in accordance with the present invention, where "H2-Citrate" denotes a citrate salt containing two free carboxyl hydrogens, and "H-Citrate" denotes a citrate salt containing one free carboxyl hydrogen.

In another embodiment in accordance with the present invention a copolymer of citric acid with D-sorbitol and starch was synthesized.

II. Copolymer of L-Aspartic Acid and D-Sorbitol

In an embodiment in accordance with the present invention copolymers of L-aspartic acid and D-sorbitol were synthesized in the presence or absence of a catalyst. Further, in the embodiment of polymerization in the presence of a catalyst, acid catalyst or base catalyst may be used in accordance with this invention.

In another embodiment in accordance with the present invention a copolymer of L-aspartic acid with D-sorbitol and starch was synthesized. Additional acids may include adipic acid, ittaconic acid and succinic acid, their anhydrides and salts thereof. Additionally, heterogeneous catalysts, such as clays, preferably, acid clays may be used in accordance with the present invention.

Thermal Synthesis of a Copolymer of L-Aspartic Acid and D-Sorbitol in the Presence of Acid Catalyst.

It is believed that copolymers of L-aspartic acid with D-sorbitol have not been reported to date. Further, although Applicants do not wish to be bound to any particular theory, they think that a key difference between the thermolytic synthesis of the present invention and the enzymatic synthesis using D-sorbitol is that in the enzymatic systems primarily only the 1' and 6' hydroxyl groups are reactive, fixing the ideal di-acid to sorbitol ratio at 1, and forming polymers that are water soluble up to Mw of 117 Daltons. In the thermolytic polymerization in accordance with the present invention, it is possible for other ratios of di-acid to sorbitol to react. Using a simple form of the Carothers equation, and assuming that all 6 of the hydroxyls on the sorbitol are available for reaction (and also assuming anhydrosorbitol sugar ring formation), the expected gel point ratios can be calculated for ratios of di-acid to D-sorbitol from 1:1 to 5:1. Gelation is expected at 100% (1:1 ratio), 75% (2:1), 66% (3:1), 83% (4:1), and 100% (5:1) rea $$\text{Gel point} = \frac{2}{\frac{\text{Reactable equivalents of acid + alcohol groups}}{\text{Total mols (diacid and alcohol)}}}$$

Preferred ratios of L-aspartic acid to D-sorbitol in accordance with the present invention are from 1:1 to 10:1, preferably from 1:1 to 5:1, including all increments within this range.

Any acid catalyst may be used in accordance with this embodiment of the present invention. Preferred acid catalysts include, but are not limited to phosphoric acid and polyphosphoric acid.

Thermal Synthesis of a Copolymer of L-Aspartic Acid and D-Sorbitol in the Presence of Base Catalysis.

In an additional embodiment in accordance with the present invention the copolymerization of L-aspartic acid with D-sorbitol is carried out in the presence of a base catalyst. The addition of a base, such as aqueous ammonia ($NH_4OH$) or NaOH to the reaction enhances the reaction in two different ways, shown schematically below as (A) and (B), respectively. It enhances the solubility of L-aspartic acid in the molten D-sorbitol solution by forming the ammonium salt. It also serves to partially deprotonate the hydroxyl groups on the sorbitol increasing their nucleophilic character, and increasing the graft to the polysuccinimide ring. The presence of the base also causes enhancement of grafting by both of these methods. These results suggest that the solubilization, especially as the labile ammonium salt, is the dominate pathway in the building of higher Mw compounds.

Scheme 2

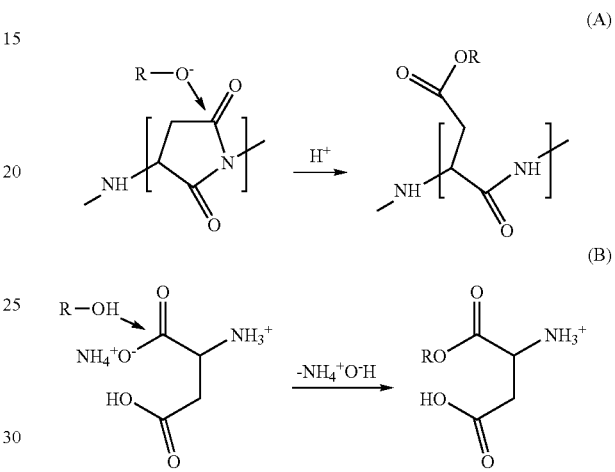

Any base may be used as a catalyst in accordance with the present invention. Preferable base catalysts in accordance with the present invention include, but are not limited to sodium hydroxide and aqueous ammonia ($NH_4OH$).

III. Copolymer of Succinic Anhydride with L-Aspartic Acid and D-Sorbitol

In another embodiment in accordance with the present invention copolymers were formed containing succinic anhydride with L-aspartic acid and D-sorbitol. Preferably, the ratio of L-aspartic acid to D-sorbitol is from 1:1 to 1:6, more preferably from 1:2 to 1:4. Preferably the amount of D-sorbitol added to the above mixtures of succinic anhydride with L-aspartic acid is in the range of from 1 to 15 wt %, more preferably from 1 to 5 wt %; most preferably the amount of D-sorbitol equals the amount of succinic anhydride in the compositions. The polymerization may take place in accordance with the present invention in an oven, in an extruder or a sigma-blade mixer.

IV. Copolymer of Succinic Anhydride with L-Aspartic Acid and Adipic Acid

In another embodiment in accordance with the present invention copolymers of succinic anhydride with L-aspartic acid and adipic acid were formed. Surprisingly, by adding 5 wt % adipic acid compositions of succinic anhydride to L-aspartic acid with molar ratio of 1:10 and 1:20 were achieved. Preferably the ratio of succinic anhydride to L-aspartic acid are at a ratio of from 1:1 to 1:30 including all increments within this ratio, more preferably at a ratio of from 1:8 to 1:20. Preferably, the amount of adipic acid is from 1 wt % to 10 wt % based on the combined amount of the succinic anhydride and L-aspartic acid including all increments within this range, more preferably from 1 to 5 wt %. The polymerization may take place in accordance with the present invention in an oven, in an extruder, such as List extruder or in a mixer, such as a sigma blade mixer or Littleford mixex.

EXAMPLES

Obviously, numerous modifications and variations of the present invention are possible in light of the above teachings. It is therefore to be understood that within the scope of the appended claims, the invention may be practiced otherwise than as specifically described herein.

1. Solvent Free Synthesis of D-Sorbitol and Citric Acid

Copolymers were synthesized using a solvent free synthesis, in which the D-sorbitol was first melted, then the citric acid was stirred in. The mixture was then placed in a vacuum oven and the temperature increased to 110° C. or 150° C. The condensation reaction was followed by sampling the system and performing a titration analysis. A plot of the results (FIG. 1) shows that the reaction is significantly faster at the higher temperature.

Using a 3:1 molar ratio of citric acid to D-sorbitol, the acidity of the mixture decreased from the theoretical value of 11.9 (mili-equivalents of acid/g of material) to a value of 0.6 (mili-equivalents of acid/g of material) demonstrating nearly complete reaction of the acid groups. The material also changed during this time from a completely water soluble sticky solid into a partially insoluble yellow solid.

Figure 2:
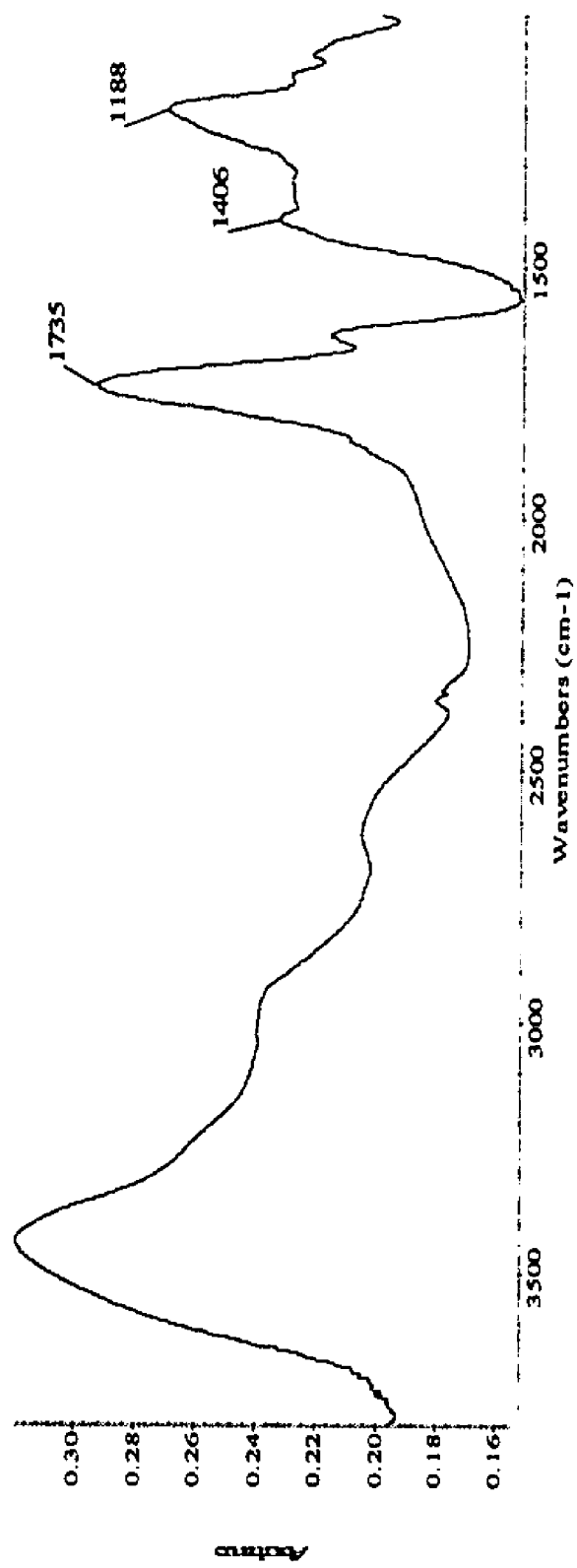
FIG. 2. The IR spectrum of a copolymer synthesized from a 3/1 citric acid and D-sorbitol molar mixture under vacuum at 150° C. overnight.

The reactions were also studied utilizing IR spectroscopy. The spectra give insight, with the peaks expected for a citrate ester of a carbohydrate. Bands at 0735 $cm^{-1}$ and 1188 $cm^{-1}$ are assigned to the ester C=O stretch and bend, respectively (FIG. 2).

Using D-sorbitol and citric, materials were synthesized utilizing multiple molar ratios of citric acid/D-sorbitol ranging from excess hydroxyl groups (1:1 citric acid/D-sorbitol) to equal molar acid and hydroxyl groups (3:1 citric acid/D-sorbitol; assuming no sugar anhydride formation) to a large excess of acid groups (6:1 citric acid/D-sorbitol).

TABLE 1

The observed residual acid, water absorbance index (WAI) and water solubility index (WSI) of polymers synthesized at 150° C.

| Citric acid/ D-sorbitol | Residual acid (m equiv/g) | Percentage of acid reacted | In Water WAI | In Water WSI | Adjusted to pH 7 WAI | Adjusted to pH 7 WSI |
|---|---|---|---|---|---|---|
| Dry Synthesis: 4 hour reaction time | | | | | | |
| 1/1 | 2.6 | 68 | 3.4 | 66 | 2.9 | 96 |
| 2/1 | 3.9 | 63 | 5.1 | 51 | 11.8 | 64 |
| 3/1 | 6.9 (±0.7) | 42 (±6) | 6.0 (±1.1) | 54 (±8) | 9.4 (±2.6) | 73 (±11) |
| 4/1 | 9.5 | 25 | Soluble | 100 | Soluble | 100 |
| 5/1 | 10.2 | 22 | Soluble | 100 | Soluble | 100 |
| 6/1 | 10.8 | 21 | Soluble | 100 | Soluble | 100 |
| Wet Synthesis: 2 hour reaction time | | | | | | |
| 3/1 | 5.0 (±0.9) | 58 (±7) | 4.7 (±1.8) | 39 (±14) | 8.7 | 39 |
| Wet Synthesis: 4 hour reaction time | | | | | | |
| 3/1 | 3.8 (±0.1) | 67 (±1) | 2.8 (±0.5) | 24 (±4) | 7.4 (±1.3) | 34 (±5) |

Materials with even higher swell ratio were achieved by neutralization and separation of the soluble material from the insoluble gel. Using a batch of the 3:1 ratio of citric acid to D-sorbitol material, the gel was suspended in a large excess of water and the pH adjusted to 7 with NaOH solution. The gel was separated out by centrifugation and the resulting solid was freeze dried. The swell ratio was tested using a 200 mesh sieve and a result of about 17 was attained.

Figure 3:
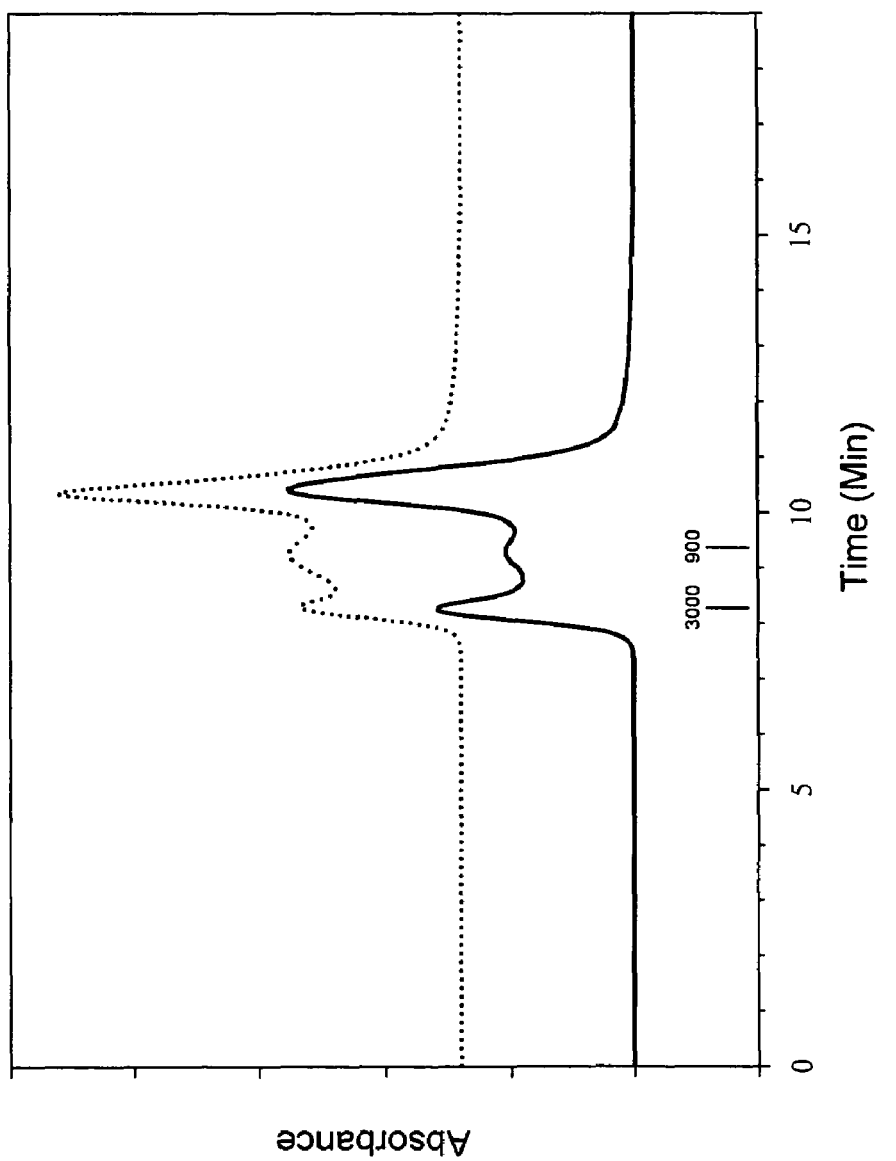
FIG. 3. A GPC chromatograms (normalized and offset for clarity) of the soluble material produced from the polymerization of a 5/1 molar ratio mixture of citric acid and D-sorbitol with reaction times of 2 hrs ( _ _ _ ) and 4 hrs ( ___ ). (See the experimental section for chromatography conditions.) The GPC shows an increase in the amount of higher MW material in the longer reaction, from ~14% to ~24% of the total peak area.

Further insight into the swelling behavior was gained by studying the soluble samples. Gel permeation chromatography (GPC) analysis of the polymers synthesized using the 5:1 ratio of materials at 2 hours and at 4 hours, both of which were completely water soluble (FIG. 3). The results show a building of the material with a peak maximum molecular weight of about 3000 Daltons and additional material with a Mw about 900 Daltons. Overall, these chromatograms demonstrate that at least 40% of the material has shown some molecular weight building to a level ≧900 Daltons, while maintaining water solubility. This corresponds to a polymer with at least 5, and as many as 16 citric acid moieties or D-sorbitol monomer units. Chromatographs of the soluble polymers made using a 4:1 or 6:1 molar ratio also show similar results.

Figure 4:
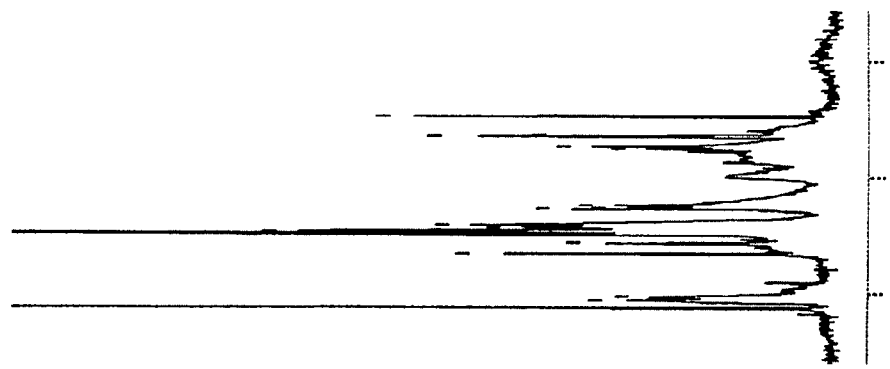
FIG. 4. The carbonyl region of the $^{13}$C NMR spectrum of a $D_2O$ solution of a polymer made using a 5/1 ratio reaction. The 2 large peaks at 175.6 and 172.4 ppm (this peak was truncated for clarity) can be assigned to citric acid. Numerous sets of other peaks are observed slightly upfield of the citric acid peaks, as expected for citric esters.

Examination of the carbonyl regions of the $^{13}C$ NMR spectra of $D_2O$ solutions of soluble samples (150° C., 3 hour reaction time, FIG. 4) supports the GPC. About 50% of the signal intensity in the carbonyl region is comprised of two signals at 175.6 and 172.4 ppm. These peaks are in the expected 1:2 ratio and near the literature values for unreacted citric acid. A series of smaller peaks, shifted slightly up field by 1 to 2 ppm from the 172.4 and 175.6 peaks, are also evident. A similar result can be obtained from looking at the CH region of the spectra, where the unreacted citric acid at 42.7 ppm also corresponds to about 50% of the total peak intensity of the region. As predicted, there are several signals shifted up field by 1 to 3 ppm corresponding to citrate esters. Similar results were also obtained from the soluble 6:1 ratio system, although the amount of unreacted citric acid contributes about 67% of the peak intensity.

2. Aqueous Synthesis D-Sorbitol-Citric Acid Copolymers

As a control experiment, we also synthesized a copolymer using a 3:1 molar ratio of citric acid to D-sorbitol, but first dissolving the reactants in water. Citric acid and D-sorbitol were dissolved in a minimal amount of water, and then dried in a force air oven at 80° C. overnight. The resulting solid was ground, then polymerized under vacuum at 150° C. The resulting polymer displayed a water absorbance index (WAI) value within experimental error of the dry synthesis (Table 1). Water solubility and acid titration values show a larger extent of reaction in this system, probably due to reaction occurring during the drying process. Overall, there appears to be little advantage to using water in this system.

3. Synthesis of a Copolymer of D-Sorbitol and Sodium Citrate

Figure 5:
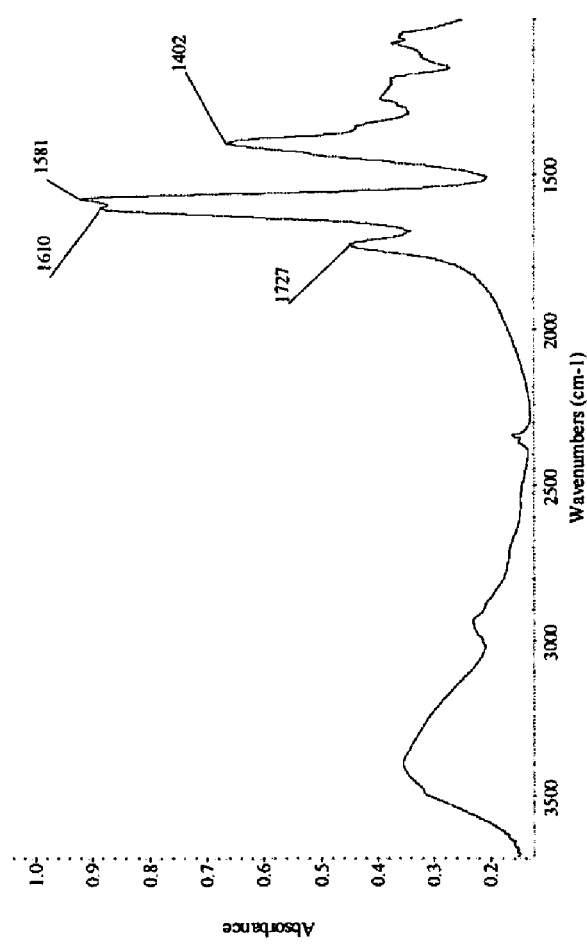
FIG. 5. The IR spectrum of a copolymer synthesized from a 3/1 disodium citrate and D-sorbitol molar mixture under vacuum at 150° C. after 20 hrs.

Mixtures utilizing the disodium or monosodium citrate salts of citric acid or mixtures thereof were used in the same manner as described above for the citric acid D-sorbitol polymerization. The D-sorbitol was allowed to melt, and then the citrate was stirred in and polymerized under vacuum at 150° C. One difference between the citric acid and the sodium citrate systems was the clarity of the melt at this stage. Citric acid and D-sorbitol form a clear viscous melt, where the sodium salts form an opaque paste under the polymerization conditions. Molar ratios of 2:1 and 3:1 citrate salt to D-sorbitol were implemented. The resultant polymers were soluble, and they contained a considerable amount of residual acid. The IR spectrum of the products (FIG. 5) shows the expected C=O stretch peak at 1727 cm$^{-1}$. Additionally, there were large 1581 cm$^{-1}$ and 1402 cm$^{-1}$ absorbances similar to those previously assigned to the carboxyl anion antisymmetrical and symmetrical stretching modes in citric acid/carbohydrate composites.

Figure 6:
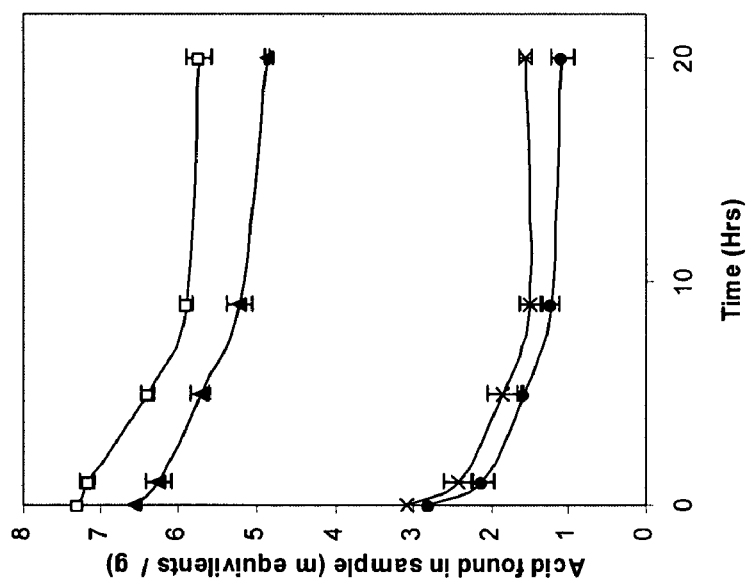
FIG. 6. The amount of acid in the sample found by titration analysis of samples taken during the polymerization of monosodium and disodium citrate polymers ran at 150° C. disodium citrate/D-sorbitol 3/1 (x); disodium citrate/D-sorbitol 2/1 (●); monosodium citrate/D-sorbitol 3/1 (□); monosodium citrate/D-sorbitol 2/1 (▲). (The error was determined from multiple analyses of the same samples.)

The reactions were sampled and titrated for residual acid content (FIG. 6). The acid content of the samples decreases as the reaction progresses. However, after about 9 hours of reaction, there is no further loss of acidity in these systems suggesting that further polymerization is not taking place. Additionally, these samples were all soluble with the exception of a small amount of insoluble material after 20 hours of polymerization. This is in contrast to the swellable network polymers observed in the citric acid-D-sorbitol polymerization described above.

TABLE 2

The amount of calcium ions sequestered by the polymer at pH7 (mmol CA$^{+2}$ sequestered per g sample). The determination was performed by titration of a sample with a CaCl$_2$ solution and the endpoint determined with a calcium ion selective electrode.

| Sample | mmol Ca$^{+2}$/g sample |
|---|---|
| citric acid/D-sorbitol copolymer (5/1 molar ratio; 4 hour reaction) | 0.65 (±0.06) |
| citric acid/D-sorbitol copolymer (4/1 molar ratio; 4 hour reaction) | 0.63 (±0.06) |
| monosodium citrate/D-sorbitol copolymer (3/1 molar ratio; 9 hour reaction) | 0.56 (±0.12) |
| monosodium citrate/D-sorbitol copolymer (2/1 molar ratio; 9 hour reaction) | 0.45 (±0.11) |
| disodium citrate/D-sorbitol copolymer (3/1 molar ratio; 9 hour reaction) | 0.35 (±0.04) |
| disodium citrate/D-sorbitol copolymer (2/1 molar ratio' 9 hour reaction) | 0.33 (±0.12) |
| citric acid alone (control experiment) | 1.3 |

Materials

The following were used as received: D-sorbitol (Sigma, 98%), sodium hydroxide standard solution (Sigma 1.0 N), sodium chloride (NaCl; Fisher, certified ACS), Citric Acid (Aldrich 99%), Sodium Dihydrogen Citrate (Aldrich, 99%), Sodium Hydrogen Citrate Sesquihydrate (Aldrich, 99%), Calcium Chloride Dihydrate (CaCl$_2$, Fisher, certified ACS), Calcium Standard solution, (Cole-Parmer Calcium Standard, 1000 ppm CaCl$_2$, Ionic Strength Adjuster (Cole-Parmer ISA 4 M KCl).

Instrumentation and Equipment

A Napco 5851 vacuum oven with a Welch W series 3 vacuum pump was used for polymerization reactions. Infrared spectroscopy was carried out on a Thermonicolet Avatar 370 spectrophotometer using transmission sample holder and standard potassium bromide pellets. Gel Permeation Chromatography (GPC) was performed on a Waters 1525 HPLC system with a Waters 717 plus autosampler and a Waters 2996 photodiode array detector and analyzed at 218 nm. A Phenomonex Poly-sep-GFC-P2000 column was used. NMR was performed on a Bruker Avance 500 NMR operating at 500 MHz for $^1$H and 125 mHz for $^{13}$C. Bruker Icon NMR software was used running on an HPx1100 Pentium 4 workstation. Peaks were referenced to sodium 3-trimethylsilylpropionate-2,2,3,3-d$_4$ (TSP) at 0.0000 ppm. Simulations of $^{13}$C NMR spectra were performed by ACD/CNMR predictor version ACD/Labs 6.00, running on a Gateway Pentium 4 CPU with a 2.53 GHz processor. Ca$^{+2}$ titrations were performed with a Corning pH/ion analyzer 350 and a Cole-Parmer 27502-09 electrode used according to the manufacturers directions without the use of ionic strength adjuster.

Analysis of Samples

Samples were analyzed for molecular weight by GPC, for water absorbance index (WAI), water solubility index (WSI), acid content and Ca$^{+2}$ by known methods in the art.

Synthesis of Polymers

A measured amount of D-sorbitol was melted in a glass beaker. The appropriate amount of citric acid or sodium citrate salt was stirred in. The beakers were placed inside of a vacuum oven and the polymerizations were run at 110° C. or 150° C. A vacuum of 30 in Hg was maintained except for the removal samples for analysis.

Signa-Blade Mixer Reactions (w/vac.)

Reactions were conducted using a Readco sigma blade mixer, 1-½ quart capacity. Mixer jacket was heated with hot oil at about 106° C. The mixer speed was about 80 rpm. Sorbitol was added first to the mixer, allowed to melt for about 3 minutes then citric acid was added. Total reactants added were about 600 g. A vacuum of about 26 mm Hg was applied to the mixer during the reaction and water was collected with a condenser cooled by dry ice. Internal temperature of the molten reactants was about 140° C. After 3 hours, sorboucitric acid polyester was removed from the reactor, allowed to cool into a hard solid, and subsequently pulverized. The residual acid was determined by stirring 1 g of polymer in 50 g distilled water, then titrating to pH 7 using 0.2 M NaOH. Starting acid values are given in parentheses in the table below. Differences between these values represent the amount of ester formed. Water solubility and gel absorption were determined by suspending 0.5 g of polymer in 50 ml distilled water, titrating to pH 7 with 1 M NaOH, then pouring the suspension over a preweighted 200 mesh wire screen and letting drain for about 2 minutes. Water absorption index (WAI) is weight of gel/weight of dry polymer. Water solubility index (WSI) is the weight of oven dried filtrate/weight of dry polymer multiplied by 100. A larger quantity of the dried gel and soluble fractions were prepared by centrifuging the pH 7 suspension at 3,000 rpm for 4 minutes, then freeze drying the soluble supernatant and insoluble gel fractions. WAI for the dried gel fraction was then measured in distilled water (WAIg) and 0.15 M NaCl (0.9% by weight NaCl). The saline absorption of a sample was found to have a value of 24. This is close to values of 40-60 for commercial cross-linked polyacrylic acid superabsorbents. It is rather surprising that a condensation polymer which is probably highly branched as sorbitol/citric acid would have such high water absorbency. The results are shown in Table 3.

TABLE 3

| Sorbitol (mol) | Citric Acid(mol) | Temp, time | Appearance | Acid (meq/g) | WSI (pH 7)* | WAI (pH 7)* | WAIg (pH 7)* |
|---|---|---|---|---|---|---|---|
| 1 | 2 | ~140 C., 3 h | leathery (hot) | 6.4 (10.6) | 75 | 15.1 | 60 |
| 1 | 3 | " | leathery (hot) | 7.1 (11.9) | 71 | 15.8 | 54, 25 w/saline |
| 1 | 4 | " | syrupy (hot) | 10.7 (12.7) | 100 | — | — |
| 1 | 5 | " | syrupy (hot) | 11.2 (13.1) | 100 | — | — |

*Using 200 mesh screen for WAI
Colors off-white to slightly yellow

Vacuum Oven Reactions

These small scale reactions were conducted to determine if starches could be added to the sorbitol/citric system to further increase water absorption. Star-dri 5 is an acid hydrolysed starch (dextrin) with an Mn of about 4000. Reactants (total of about 35 g) were added to 600 ml beakers and placed in a vacuum oven set at 160° C. Reactants were removed and stirred every ½ hour until the 2 hour time when the mixtures became elastic. Samples were removed from oven, allowed to cool, and ground with a mortar and pestle. WSI and WAI were determined as above except that gel and sol fractions were separated by centrifugation. WAIg values were calculated from the equation:

WAIg=WAI/WSI×100.

The results are shown in Table 4 below.

Twin-Screw Extruder Reactions

The reaction was allowed to occur very quickly (3-4 min) due to high temperatures and easy release of water of condensation resulting from the thin layer of reactants on screw flights. The extruder was a Werner-Pfleiderer ZSK-30, with a 30 mm diameter barrel, 42×30 mm long. The reactants were dry mixed then fed into the barrel section 1 using a loss-weight feeder. Barrel sections 9-10 and 13 were open to allow release of water of condensation. Segment 1 was at room temperature (feed throat), while the segments 2-3 were maintained at 200° F., process temperature was maintained in segments 4-14. Based on residual acid values, very high degree of esterifications were achieved for sorbitol/sodium citrate reactions. There was excess acid present in sorbitol/citric 1/4 so as to prevent cross-linking. The results are shown in Table 5 below.)

TABLE 4

| Sorbitol (mol) | Star-dri 5 (mol) | Citric acid (mol) | Temp, time | Appearance | Acid (meq/g) | WSI (pH 7)* | WAI (pH 7)* | WAIg (pH 7)* |
|---|---|---|---|---|---|---|---|---|
| 0.5 | 0.5 | 2 | ~150 C., 3 h | leathery (hot) | 7.1 (10.6) | 74 | 8.1 | 31 |
| 0.5 | 0.5 | 3 | " | leathery (hot) | 9.3 (11.9) | 71 | 5.4 | 19 |
| 0.5 | 0.5 | 4 | " | leathery (hot) | 10.5 (12.7) | 89 | 5.3 | 48 |
| 0.5 | 0.5 | 5 | " | leathery (hot) | 11.9 (13.1) | 100 | 4.1 | ☐ |

*Using centrifuge method
Colors were off white to slightly yellow

TABLE 5

| Sorbitol (mol) | Citric Acid (mol) | Na$_2$HCitrate.1.5 H$_2$O (mol) | NaH$_2$Citrate (mol) | Temp. (C.) | Screw speed (rpm) | Feed rate (lb/min.) | Sample Appearance | Acid (mEq/g)* |
|---|---|---|---|---|---|---|---|---|
| 1 (364 g) | 4 (1536 g) | | | 180 | 75 | 0.11 | yellow | 10.2 (12.7) |
| " | " | | | 180-200 | " | " | yellow | 11.4 |
| " | " | | | 200 | " | " | yellow | 10.5 |
| " | " | | | 220 | " | " | orange | 10.1 |
| 1 (728 g) | | 1 (1052 g) | | 204 | " | " | light yellow | 0.69 (2.2) |
| " | | " | | 220 | " | " | light yellow | 0.53 |
| 1 (364 g) | | 2 (1052 g) | | 220 | " | " | yellow | 0.05 (2.8) |
| " | | " | | 204 | " | " | light yellow | 0.97 |
| 1 (728 g) | | | 1 (856 g) | 204 | " | " | white | 1.1 (5.1) |
| " | | | " | 220 | 120 | 0.06 | light yellow | 0.16 |

TABLE 5-continued

| Sorbitol (mol) | Citric Acid (mol) | Na$_2$HCitrate.1.5 H$_2$O (mol) | NaH$_2$Citrate (mol) | Temp. (C.) | Screw speed (rpm) | Feed rate (lb/min.) | Sample Appearance | Acid (mEq/g)* |
|---|---|---|---|---|---|---|---|---|
| 1 (546 g) | | | 2 (1284 g) | 204 | 190 | " | off white | 0.67 (6.6) |
| 0.75 (273 g) + 0.25 corn starch (90 g) | 4 (1536 g) | | | 204 | 210 | 0.11 | orange | 11.4 (12.7) |

*Starting values of acid in parentheses

4. Thermal Synthesis of a Copolymer of L-Aspartic Acid and D-Sorbitol in the Presence of Acid Catalysis.

Figure 7:
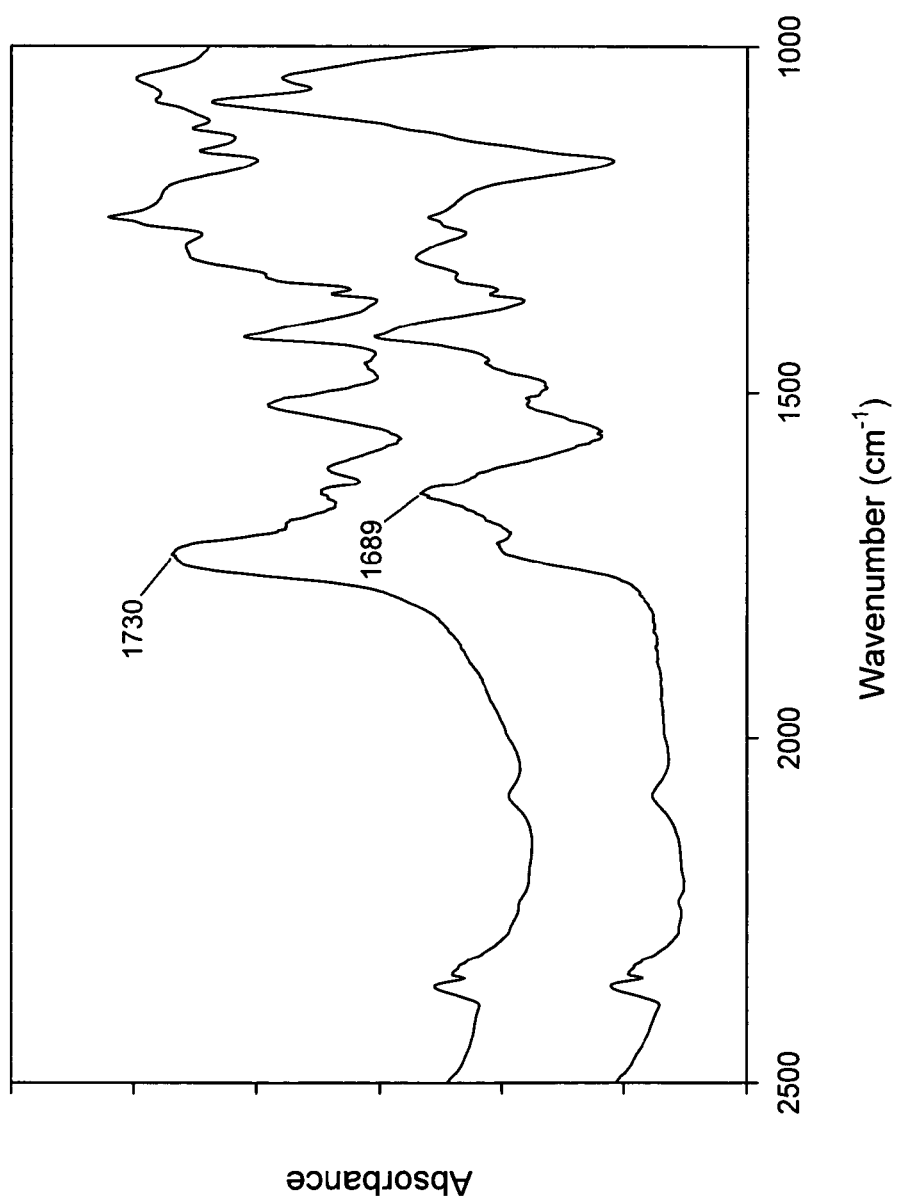
FIG. 7. The IR spectra (offset for clarity) from the reaction of L-aspartic acid with D-sorbitol with 0.5 (top), and 0.1 (bottom) equivalents of polyphosphoric acid catalyst. The emergence of an IR absorbance of ~1730 cm$^{-1}$ is indicative of sorbitol ester formation.
Figure 8:
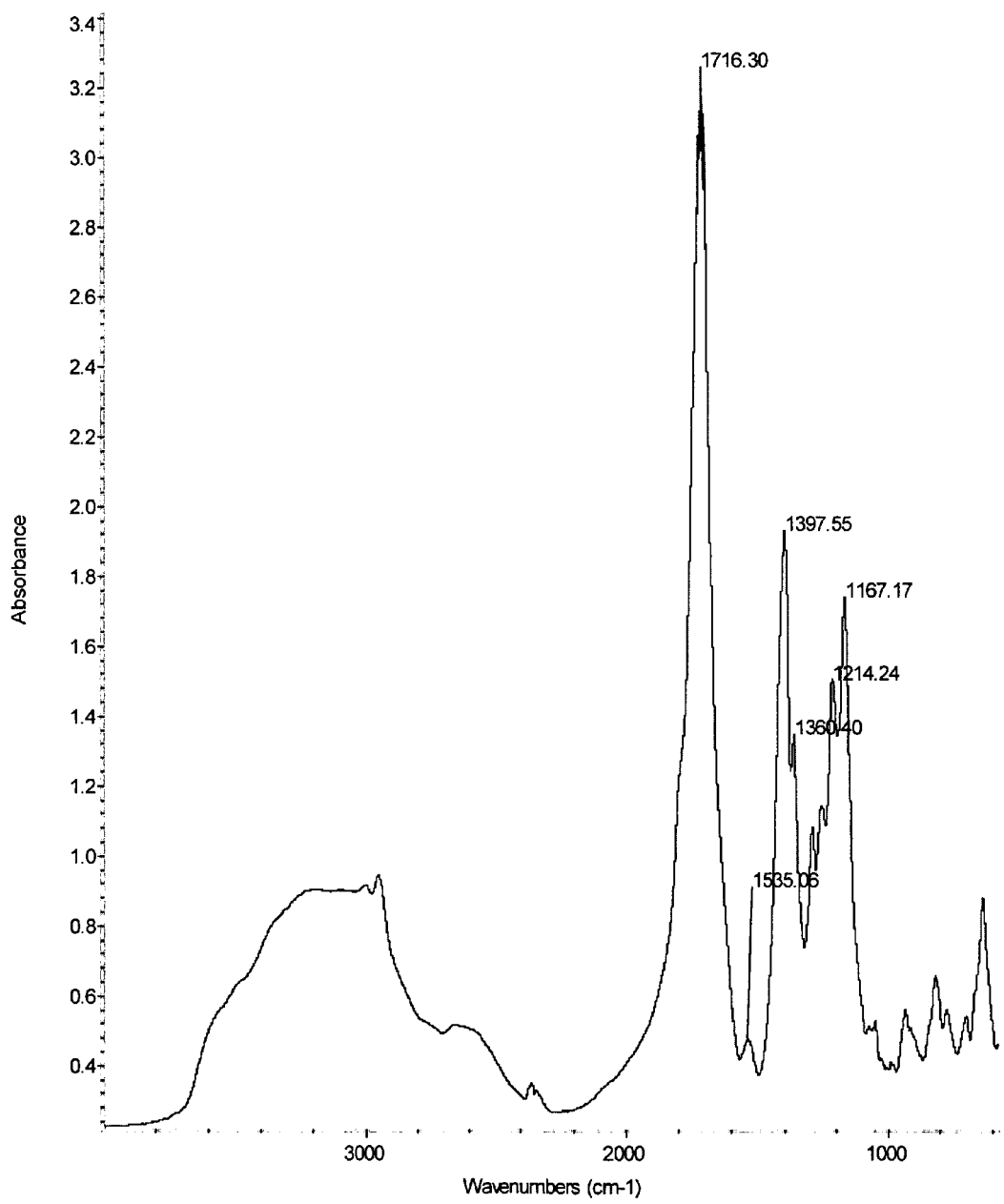
FIG. 8. FTIR spectrum of oven reaction at 200-205° C. of succinic anhydride:aspartic acid 1:2 ratio after 15 min.
Figure 9:
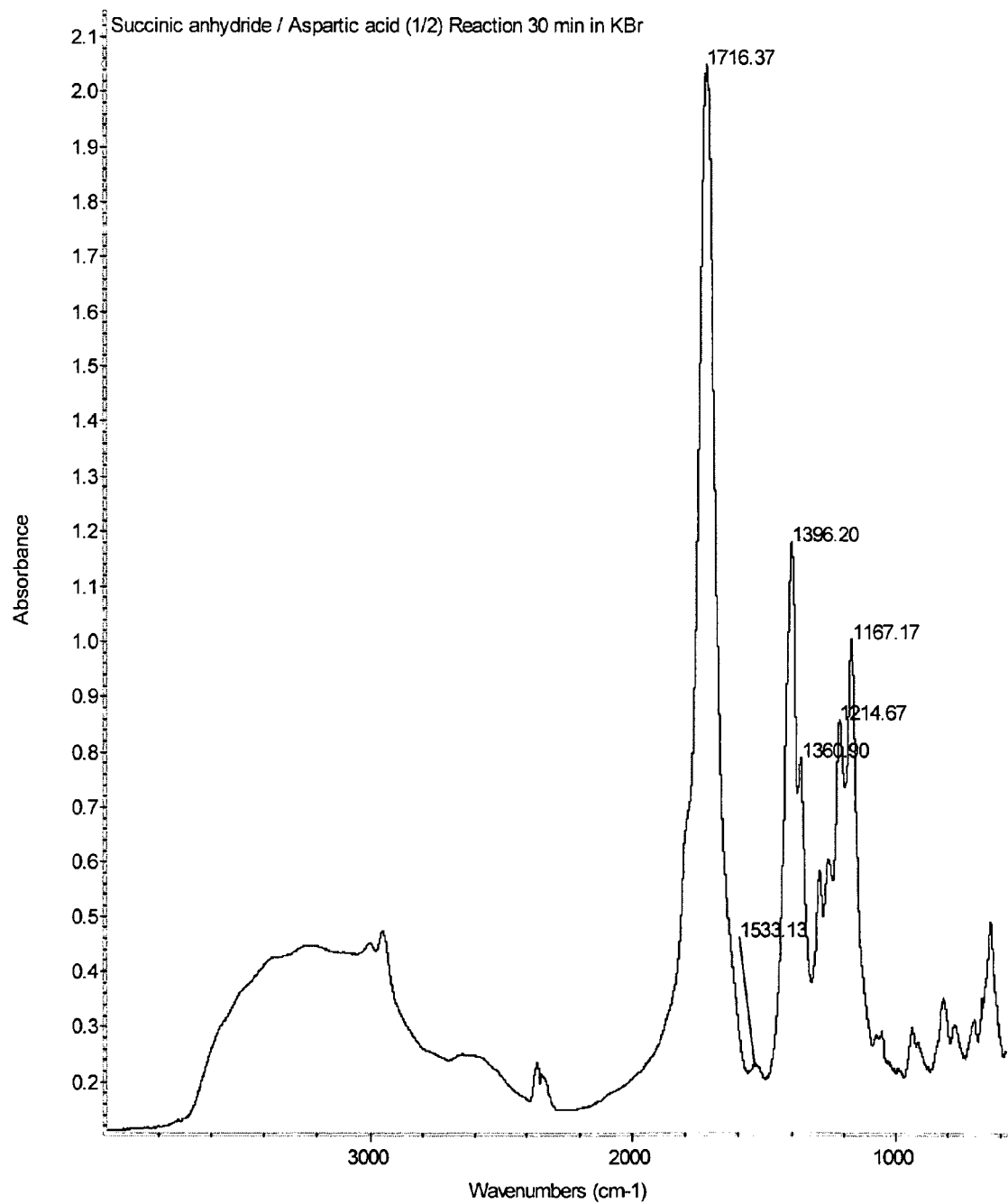
FIG. 9. FTIR spectrum of oven reaction at 200-205° C. of succinic anhydride:aspartic acid 1:2 ratio after 30 min.
Figure 10:
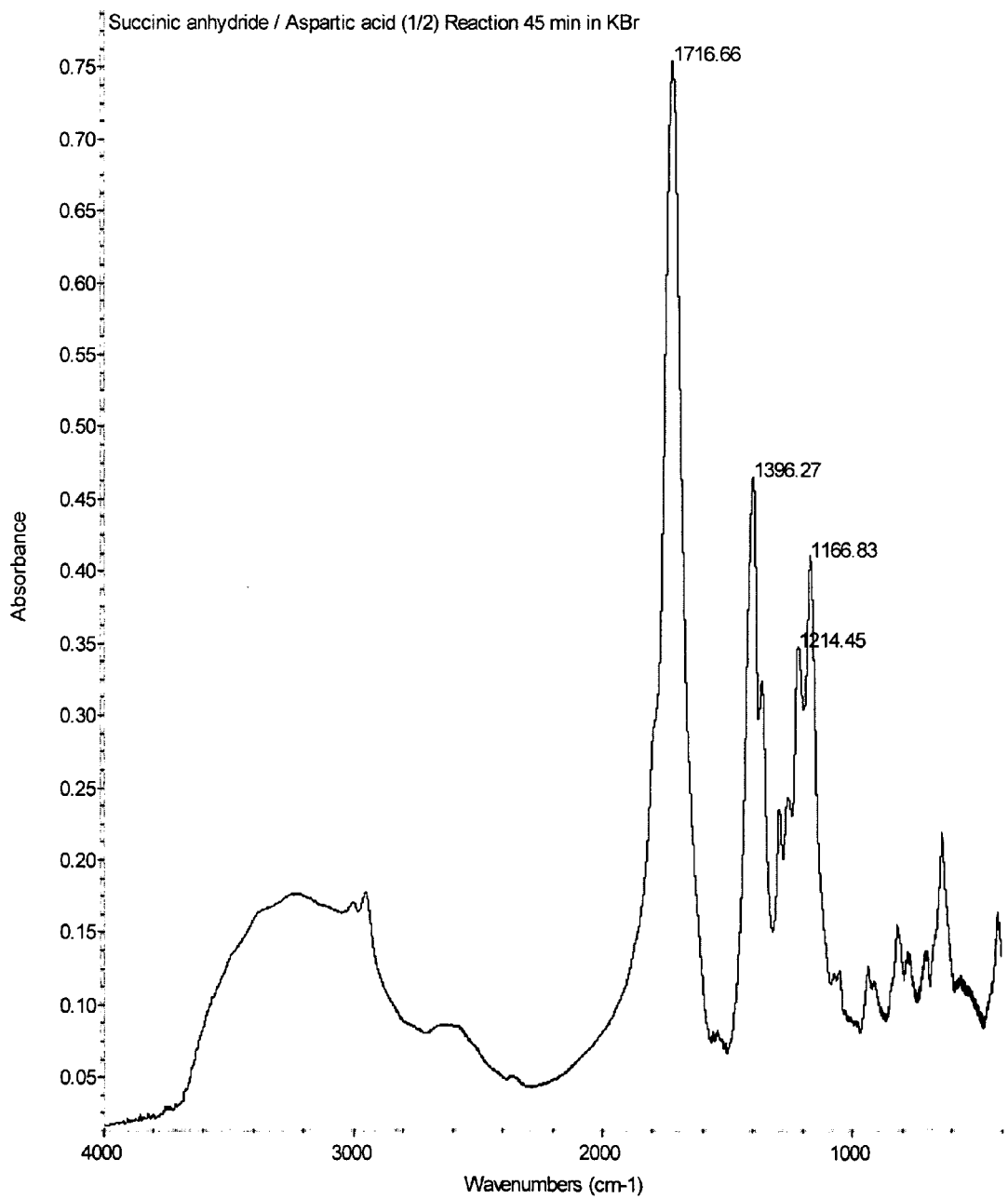
FIG. 10. FTIR spectrum of oven reaction at 200-205° C. of succinic anhydride:aspartic acid 1:2 ratio after 45 min.
Figure 11:
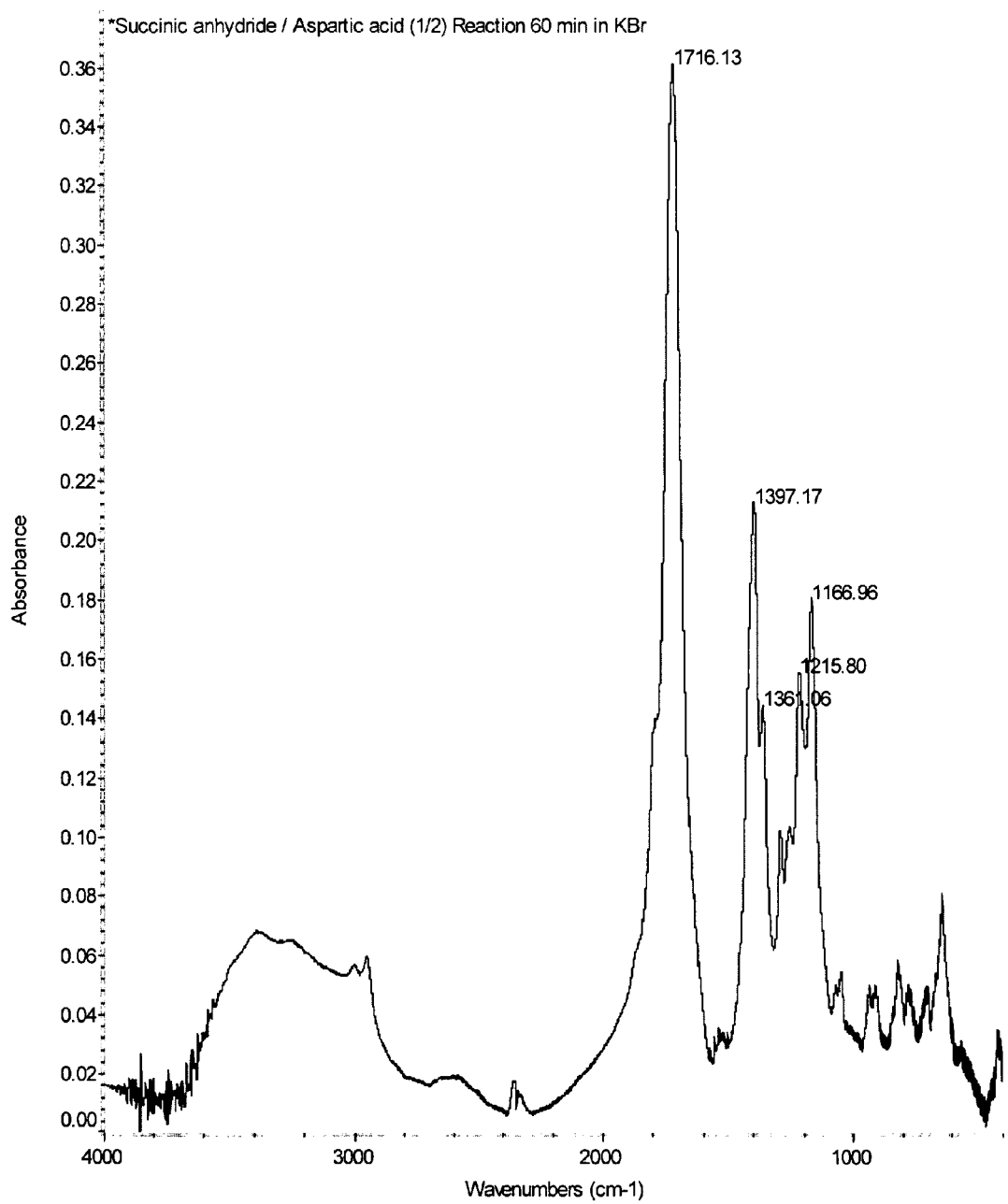
FIG. 11. FTIR spectrum of oven reaction at 200-205° C. of succinic anhydride:aspartic acid 1:2 ratio after 60 min.
Figure 12:
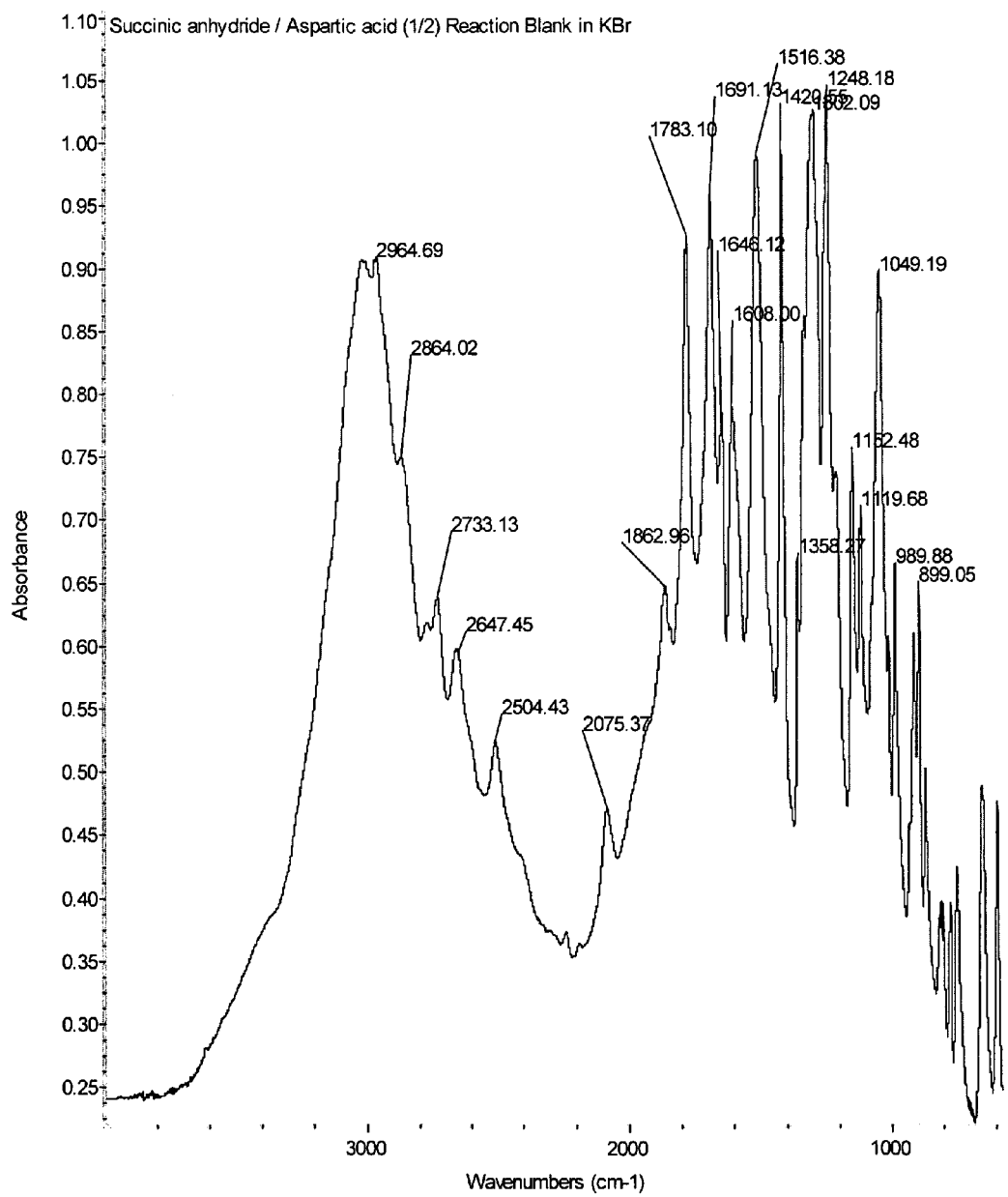
FIG. 12. FTIR spectrum for unreacted monomer mix of succinic anhydride:aspartic acid 1:2 ratio.

L-aspartic acid and D-sorbitol polymerization was performed with the addition of polyphosphoric acid catalyst at 170° C. The sorbitol was first heated to 150° C., approximately 50 degrees above its melting point of 98-100° C. This enabled us to effectively stir in the L-aspartic acid, and the catalyst. The IR spectra of three samples (FIG. 7) from a reaction of a 2:1 molar ratio of L-aspartic acid to D-sorbitol were taken. A significant increase in a broad IR absorbance band at about 1730 cm$^{-1}$, indicative of sorbitol ester formation, can be observed as the amount of acid catalyst was increased from 0.1 to 0.5 equivalents (compared to L-aspartic acid). A corresponding change in the physical appearance of the compounds can also be observed. The material synthesized with 0.52 equivalents of the catalyst, yields a product which is a homogeneous light yellow powder.

These samples were also titrated for acid content and analyzed for nitrogen by the same methods used for the previous samples. Additionally, the formation of phosphate esters is also possible in catalytic systems which contain phosphoric acid, therefore we analyzed the samples for phosphorous by methods described in the literature.

Under the conditions used in our experiments above no reaction occurred in the absence of a catalyst as evidenced by the absence of the IR band at 1730.

The acid titration values of the catalyzed reaction are similar to the values observed in the catalyst free polymerized materials. However, as the amount of catalyst added to the reaction is increased, the amount of acidic groups remaining in the product also increases. Additionally, the amount of residual phosphorous in the samples increases by nearly a factor of 10.

Interestingly, these samples display a larger water soluble fraction than the samples polymerized in the catalyst free system, with the exception of the system with 0.3 equivalents of polyphosphoric acid. Not only was this sample less soluble, but it visibly swelled when soaked in water.

GPC analysis of the sample with a low level of catalyst added is again similar to the catalyst free polymerization. However, the polymerization with catalyst shows considerable molecular weight increase, with over 30% of the materials having a Mw greater than 1000 Daltons. The fraction of material with Mw greater than 3000 Daltons also increased in the catalytic polymerization.

Further, polymerizations were performed at 200° C., using phosphoric acid or polyphosphoric acid catalyst. Homogeneous material could be synthesized using L-aspartic acid/D-sorbitol molar ratios ranging from 2:1 to 5:1. These materials showed measurable swell ratios when soaked in water or similar swell ratios using a weakly basic (0.1 M NaCO$_3$) solution, indicative of the formation of a network polymer.

5. Thermal Synthesis of a Copolymer of L-Aspartic Acid and D-Sorbitol in the Presence of Base Catalysis.

The addition of base enhances the reaction of L-aspartic acid with D-sorbitol by partially deprotonating the hydroxyl groups on the sorbitol increasing their nucleophilic character, and increasing the graft to the polysuccinimide ring. To test for the deprotonation pathway described above, first a 1:1 molar mixture of D-sorbitol and NaOH was prepared which was dried in the vacuum overnight to produce deprotonated D-sorbitol. The resulting solid was polymerized with L-aspartic acid in ratios ranging from 4:1 to 1:2 at 200° C. under vacuum. Only soluble or mostly soluble products were produced. GPC analysis found only Mw<1500 Daltons for all of these products. Similarly, the use of triethyl ammonia (Et$_3$N) as a catalyst did not give products with any apparently grafted material.

In contrast, when polymerizations using 1 equivalent of added NH$_4$OH were performed, from 4:1 to 1:2 ratios at 200° C., the resulting compounds ranged from a soluble solid, when excess sorbitol was used, to an insoluble solid, when excess L-aspartic acid was used. IR spectroscopy showed there was considerable imide formation in all of the compounds evidenced by the absorbance at 1716 cm$^{-1}$. Insoluble samples were hydrolyzed in 1 N NaOH solution at 80° C., a procedure that has been shown to open any imide rings and increase solubility of polysuccinimide (PSI). GPC analysis of the hydrolyzed product showed a considerable amount of sample with a Mw>5000 Daltons, indicating that Mw building of the amino acid branches in the system that is detectable even after probable hydrolysis of any grafted esters. GPC analysis of the soluble samples or the soluble portion of the insoluble samples did not show any significant amount of material with a Mw>1000 Daltons.

Materials

The following were used as received: L-aspartic acid (Sigma, 98%), D-sorbitol (Sigma, 98%), o-phosphoric acid 85% (H$_3$PO$_4$; Fisher NF/FCC), hydrochloric acid (HCl; Fisher, certified ACS plus), sulfuric acid (H$_2$SO$_4$; Fisher, certified ACS plus), polyphosphoric acid (Aldrich), boric acid (Fisher), ammonium hydroxide (NH$_4$OH; Fisher, certified ACS plus), ammonium molybdate ((NH$_4$)$_6$Mo$_7$O$_{24}$, 4H$_2$O; Fisher, certified ACS) sodium hydroxide (NaOH; Fisher, certified ACS), sodium hydroxide standard solution (Sigma 1.0 N), sodium chloride (NaCl; Fisher, certified ACS), sodium bicarbonate (NaHCO$_3$; Fisher, certified ACS), sodium phosphate monobasic (NaH$_2$PO$_4$H$_2$O; Fisher, certified ACS), sodium sulfite (Na$_2$SO$_3$; Fisher, certified ACS), sodium polyacrylic acid (American Polymer Standards), Tris [hydroxylmethylamino] methane (TRIS; Fisher, molecular biology grade), hydroquinone (Sigma, 99+%), triethyl amine (Et$_3$N; Sigma, 99.5%), potassium bromide (KBr; Spectra-Tech).

Instrumentation and Equipment

A Napco 5851 vacuum oven with a Welch W series 3 vacuum pump was used for polymerization reactions. Infrared spectroscopy was carried out on a Thermonicolet Avatar 370 spectrophotometer using transmission sample holder and standard potassium bromide pellets. Ultraviolet/Visible spectroscopy was performed on a Perkin Elmer Lambda 35 spectrometer. Elemental analysis was performed on a Perkin Elmer 2400 Series II CHNS/O analyzer. Gel Permeation Chromatography (GPC) was performed on a Waters 1525 HPLC system with a Waters 717 plus autosampler and a Waters 2996 photodiode array detector and analyzed at 218 nm. A Phenomenex Poly-sep-GFC-P2000 column was used. Simple titrations were performed on a Thermo Orion 95-auto-titrator.

Analysis of Samples

Samples were analyzed for molecular weight by GPC, for swell ratios, acid content and phosphorus analysis by methods known in the art.

Synthesis of Polymers

For the polymers synthesized with $H_3PO_4$, polyphosphoric acid and $NH_4OH$, a dry mixture of 1-aspartic acid and D-sorbitol in the appropriate ratios (0.1 mols of each was used in the 1:1 ratio experiments) was stirred in a glass beaker. Then an appropriate amount of catalyst was added as a liquid and the mixture stirred into a paste. The beakers were placed in a vacuum oven and the polymerizations were run for 4 hours at 200° C. under vacuum of 30 in Hg, unless otherwise specified. For catalyst free reactions, or the ones using $Et_3N$, the D-sorbitol was first heated to 150° C., at which temperature the D-sorbitol was in the molten state. The reactants were then stirred in and the mixture was polymerized as above.

The polymerization using NaOH was first accomplished by preparing an aqueous mixture of 1.50 g (0.038 mol) NaOH and 6.55 g (0.037 mol) D-sorbitol which was allowed to stir for 20 minutes. This was dried overnight in the vacuum oven. The resulting solid was polymerized with aspartic acid in the same manner as above.

6. Extruder Synthesis of a Copolymer of Succinic Anhydride with L-Aspartic Acid in the Presence of Sorbitol Initially, extruder runs were carried out of succinic anhydride and aspartic acid at 1:2, 1:3, and 1:4 molar ratios, respectively.

Extruder

A twin-screw unit which has a 30 mm barrel was used in a configuration with eight zones and two vents. The extruder was run at a feed rate of 50 g/min during most of the runs, except for a few runs where the rate was increased by 50% to see if shortened residence time would affect the product being formed.

In all the extruder reactions that were run, steam could be seen emerging from the two vents, consistent with loss of water during the reaction. This was verified by holding a circular polished disk at the port to evaluate whether the vapors emerging from the extruder vent were just water (vapor condenses on the disk and then evaporates) or succinic anhydride (vapor leaves a visible residue on the disk). At lower extruder temperatures it appeared that almost all the vapor given off was water, however as the temperature was increased some loss of succinic anhydride out of the vents was observed.

End Capped Compositions

Compositions were run at 1:2, 1:3, and 1:4 molar ratios of succinic anhydride to L-aspartic acid. The materials were pre-mixed at the solid state and subsequently placed into the hopper and fed as a powder into the extruder. 3 kg increments of material were combined at a time in a large plastic jar and shaken to mix the powders. The recipes used are shown in Table 6 below:

TABLE 6

| Molar ratio succinic:aspartic | Weight of succinic anhydride | Weight of aspartic acid |
| --- | --- | --- |
| 1:2 | 820 g | 2180 g |
| 1:3 | 601 g | 2399 g |
| 1:4 | 475 g | 2525 g |

Oven Synthesis of Compositions Run in the Extruder

For each composition that ran in the extruder, a sample was taken of the premix powder and the material was reacted in an oven. A relatively small amount of powder was placed in the bottom of a beaker and the beaker was placed into the oven. The reaction proceeded as the mixture melted and then bubbled in the bottom of the beaker. Samples were taken by briefly removing the beaker from the oven and collecting a small amount of material on a spatula for FTIR analysis.

Oven Synthesis of Succinic Anhydride:Aspartic Acid at 1:2 Ratio

The oven was operated at about 200-205° C. The mixture melted relatively rapidly, and samples for analysis were removed at 15, 30, 45, and 60 min. After grinding, all the samples were light tan in color. Most of the material was soluble in acetone but a fine white powder remained as insoluble; perhaps this is some unreacted aspartic acid. The FTIR spectra for the four samples are shown in FIGS. 9-12, and for comparison the FTIR of the starting mixture which has not been reacted is shown in FIG. 13. Thus, judged from the FTIR, the reaction proceeds well and is fairly complete even in about 15 min.

Extruder Synthesis of Succinic Anhydride:Aspartic Acid at 1:2 Ratio

At a ratio of 1:2 the mixture of succinic anhydride: aspartic acid formed a melt very readily, which could be observed at various points in the extruder. At the exit die the product emerged as a very low viscosity melt which basically dripped out the end. The above mixture was run under various extrusion conditions and samples were collected for analysis. Extruder sample #1 was collected at a temperature of 176-179° C. (350-355° F., their software works in Fahrenheit). The FTIR spectrum (FIG. 14) seemed to indicate that significant reaction had occurred, but that reaction was not complete. We then increased the temperature to 193° C. (380° F.) and continued running, collecting extruder sample #2. The FTIR spectrum (FIG. 15) shows more reaction than seen in extruder sample #1, but probably not quite as good as the 15 minute oven sample. The temperature was then increased to 199° C. (390° F.) and extruder sample #3 was collected. The FTIR spectrum (FIG. 16) looks quite good. Finally the temperature was increased to 204.5° C. (400° F.) and extruder sample #4 was collected. The FTIR spectrum for this sample (FIG. 17) also looks very good. The last run in this series was also run at 204.5° C. but the feed rate was increased by 50% to reduce the residence time of the material in the extruder. Extruder sample #5 was collected at this point, and the FTIR spectrum (FIG. 18) looks very similar to FIG. 17. So at least as far as the FTIR data can tell, the reduced residence time did not significantly change the material being produced.

In addition, at two points during this run very small samples were collected from the first vent of the extruder.

The FTIR spectra for these samples are shown in FIGS. 19 and 20. These samples showed that reaction had already occurred, but not to the extent seen for material exiting the extruder; this result is of course entirely reasonable since the material has less time and temperature exposure at the first vent.

Oven Synthesis of Succinic Anhydride:Aspartic Acid 1:4

The reaction was started around 210-220° C. and the first sample was collected at 30 min. since the mixture was slower to melt relative to the 1:2 reaction. Samples collected at 45, 60, and 90 min. were about 220° C. This ratio of reactants never formed a true melt but more like a paste which bubbled as the reaction proceeded. The FTIR spectra for the samples collected show increasing conversion. At 30 min. reaction time we see a good imide peak, but the reaction clearly is not yet complete. At 45 minutes the conversion looks better but still obviously incomplete. The 60 min. and 90 min. reaction data continue to look progressively better.

Extruder Synthesis of Succinic Anhydride:Aspartic Acid 1:4

At this ratio the mixture appeared to form a very thick melt, perhaps a little thicker than the material at 1:3 ratio. This product also emerged from the end of the extruder as a thick paste which would slowly fall into the receiving vessel. Extruder sample #6 was collected at a temperature of about 204.5° C. (400° F.). The FTIR spectrum shows that the material is better than the 60 min. oven sample and is close to the 90 min. oven sample. Extruder sample #7 was collected at a temperature of about 215.5° C. (420° F.). The Extruder sample #8 was collected at a temperature of about 226.7° C. (440° F.). The FTIR spectrum again is reasonably similar to the next lower temperature run. A somewhat larger sample of about 200 g of this material was collected. Extruder sample #9 was collected at a temperature of about 232° C. (450° F.). In total about 480 g of material corresponding to sample #9 was collected. Extruder sample #10 was also collected at a temperature of about 204.5° C. but at a 50% faster feed rate which reduced residence time.

Oven Synthesis of Succinic Anhydride:Aspartic Acid 1:3

The reaction was started around 210-220° C. and the first sample was collected at 30 min. since the mixture was slower to melt relative to the 1:2 reaction. Samples were collected at 45, 60, and 90 min. and the temperature was about 220° C. for these samples. This ratio of reactants never formed a true melt but more like a paste which bubbled as the reaction proceeded. The FTIR data show significant but incomplete reaction at 30 min. For 45, 60, and 90 min. the data appear to show pretty good conversion.

Extruder Synthesis of Succinic Anhydride:Aspartic Acid 1:3

At the 1:3 ratio the mixture appeared to form a very thick melt. The product emerged from the end of the extruder as a sort of thick paste which would fall into a receiving vessel. Extruder sample #11 was collected at a temperature of about 215.5° C. (420° F.). The FTIR spectrum shows pretty good conversion. Extruder sample #12 was collected at a temperature of about 226.7° C. (440° F.). Under these conditions we collected a larger amount of material, roughly 800 g. The FTIR spectrum also shows good conversion.

Extruder Synthesis of Succinic Anhydride:Aspartic Acid 1:4 with Addition of Sorbitol We carried out a quick experiment at the very end of our trials by adding Sorbitol just before we ran out of feed for the extruder. So sorbitol was added to a 1:4 run (226.7° C.), with the amount of sorbitol about equal to the amount of succinic anhydride. Extruder sample #14 was collected under these conditions. Then the feed rate for sorbitol was increased from 17 to 22 and another extruder sample, #15, was collected. In general, the addition of sorbitol did not make any readily obvious change to the material exiting the extruder, except at one point while the feed was being adjusted it spiked to a higher value, and it appeared the material was a little more viscous for a short time.

7. Extruder Synthesis of a Copolymer of Succinic Anhydride with L-Aspartic Acid in the Presence of Adipic Acid Extruder runs of aspartic acid and succinic anhydride at 8:1 molar ratio, were performed. By adding 5% adipic acid, we were able to further extend the molar ratio to 10:1 and then 20:1. As shown from FTIR analysis the reactions appeared to go well. The results were also veryfied with titration analysis of selected samples for each composition. We ran as high as 525° F. (274° C.) at one point, and made sustained runs at 510° F. (266° C.). One issue which we improved upon is the color of material, which can be produced by extrusion. In this trial the extruder contained all elements made of stainless steel; replacement of the final element for this trial didn't seem to have too much impact on the color of material produced at 8:1 ratio. The materials made at 10:1 and 20:1 ratio are a little darker in color, most likely due to the higher extruder temperature. When the material is quenched to lower temperature upon exiting the extruder, a material with lighter color is produced. In terms of molecular weight, the 8:1 materials were measured to have $m_p$ about 1000 Dalton. With 5% adipic acid added, we found $m_p$ about 800 Dalton for 8:1+adipic acid, $m_p$ about 1000 Dalton for 10:1+adipic acid, and $m_p$ about 2300 Dalton for 20:1+adipic acid.

Extruder

We used the same configuration described above of the extruder for this trial, namely, a twin-screw unit which has a 30 mm barrel. The extruder was run at a feed rate of 50 g/min as in the first trial. Once again, steam could be seen emerging from the two vents, consistent with loss of water during the reaction. In addition, we also lost some succinic anhydride out of the vents as evidenced by observation of some crystals forming at the exit of the vent.

End Capped Compositions

Compositions of 8:1, 10:1, and 20:1 molar ratios of aspartic acid to succinic anhydride were polymerized, the latter two including 5% adipic acid. The 8:1 ratio was essentially a repeat of runs made before and the 10:1 and 20:1 ratios were new experiments. We made solid pre-mixes which were put into the hopper and fed as a powder into the extruder. It was necessary to screen the succinic anhydride to remove clumps before mixing. We generally mixed 3 kg of material at a time in a large plastic jar and shook it 50 times to mix the powders. Pre-mixed component batches were made and fed into the primary feeder. The recipes used were as follows:

TABLE 7

| Molar ratio aspartic acid:succinic anhydride | Weight of succinic anhydride | Weight of aspartic acid | Weight of adipic acid |
|---|---|---|---|
| 8:1 | 258 g | 2742 g | — |
| 8:1 + 5% adipic acid | 165 g | 1735 g | 100 g |
| 10:1 | 210 g | 2790 g | — |

TABLE 7-continued

| Molar ratio aspartic acid:succinic anhydride | Weight of succinic anhydride | Weight of aspartic acid | Weight of adipic acid |
|---|---|---|---|
| 10:1 + 5% adipic acid | 195 g | 2580 g | 145 g |
| 20:1 + 5% adipic acid | 70 g | 1830 g | 100 g |

After milling to a fine powder the color of most of the samples looked like some grade of light tan to a little darker tan or yellowish tan in color; the variations in color of the solid materials before milling is sometimes "lost" to some extent via the milling process.

The samples collected during the two days of runs are listed in the following table.

TABLE 8

| Sample Composition | Extruder Temperature (° C.) |
|---|---|
| 8:1 aspartic acid:succinic anhydride | 243 |
| 8:1 aspartic acid:succinic anhydride | 243→254 |
| 8:1 aspartic acid:succinic anhydride | 254 |
| 10:1 aspartic acid:succinic anhydride, collected at vent 9 | ??? |
| 8:1 aspartic acid:succinic anhydride | 254 |
| 8:1 aspartic acid:succinic anhydride | 254→266 |
| 8:1 aspartic acid:succinic anhydride | 266 |
| 8:1 aspartic acid:succinic anhydride | 266→274 |
| 8:1 aspartic acid:succinic anhydride | 274 |
| 8:1 aspartic acid:succinic anhydride + 5% adipic acid | 266 |
| 8:1 aspartic acid:succinic anhydride + 5% adipic acid | 266 |
| 8:1 aspartic acid:succinic anhydride + 5% adipic acid | 266 |
| 8:1→10:1 aspartic acid:succinic anhydride + 5% adipic acid | 266 |
| 10:1 aspartic acid:succinic anhydride + 5% adipic acid | 266 |
| 10:1 aspartic acid:succinic anhydride + 5% adipic acid | 266 |
| 10:1 aspartic acid:succinic anhydride + 5% adipic acid | 266 |
| 10:1→20:1 aspartic acid:succinic anhydride + 5% adipic acid | 266 |
| 20:1 aspartic acid:succinic anhydride + 5% adipic acid | 266 |
| 20:1 aspartic acid:succinic anhydride + 5% adipic acid | 266 |
| 20:1 aspartic acid:succinic anhydride + 5% adipic acid | 266 |

Oven Synthesis of Aspartic Acid:Succinic Anhydride 8:1 with Added Adipic Acid

In order to determine the effect of adipic acid on the reaction of aspartic acid and succinic anhydride prior to contacting experiments at the extruder with this system, we made up a set of three reactions in beakers and placed them in a vacuum oven (low vacuum of about 5 inches) at high temperature (of about 220° C.) for one hour reaction time. We placed three samples in the oven as follows: a control sample of 8:1 aspartic acid:succinic anhydride, a sample at the same ratio material but with 10% adipic acid added and a sample at the same ratio of aspartic acid: succinic anhydride but with 20% adipic acid added. We checked the physical state of the samples after one hour. The control sample was pretty powdery in nature. The sample with 10% adipic acid added was much more fluid and had the consistency of a thick paste. The sample with 20% adipic acid had formed what appeared to be a true melt, albeit a thick one, which flowed very slowly when the beaker was tilted. FTIR data show that significant reaction has taken place, but it appears the reaction is not complete in one hour. We noted that the imide peak appeared to have shifted in the sample with 20% adipic acid. The peak maximum is at 1716 cm$^{-1}$ for the sample with no adipic acid, at 1717 cm$^{-1}$ for the sample with 10% adipic acid, and at 1700 cm$^{-1}$ for the sample with 20% adipic acid. On the basis of this range finding study, we decided to try running the extruder at 5% or 10% adipic acid as needed to keep the extruder torque from getting too high as we extended the ratio of aspartic acid to succinic anhydride.

Extruder Synthesis of Aspartic Acid:Succinic Anhydride 8:1 and 8:1+5% Adipic Acid Extrusion was first performed at the feed ratio of 8:1 of aspartic acid to succinic anhydride at a temperature of 243° C. (470° F.). Once again the product came out of the extruder as an extremely thick paste which had to be scraped off the exit with a putty knife. The 8:1 material at this temperature had a tan color. We collected Samples #20-28 during the 8:1 ratio run, as we varied the extruder temperature from 243° C. to 254° C. to 266° C. and finally to 274° C. FTIR spectra show a strong imide peak and are similar to one another; one difference compared to lower ratio material which we continue to see is that the shoulder which is assigned to anhydride at around 1799 cm$^{-1}$ is a bit more resolved and intense in the 8:1 ratio material. Samples prepared at 8:1 ratio of aspartic acid to succinic anhydride, and prepared under different conditions did not exhibit any meaningful differences. Looking at the molecular weight data, we see that the Mw of the 8:1 samples are about 1000 Dalton. When 5% adipic acid is added to the 8:1 composition, the molecular weight drops to about 800, so it appears that for some reason the molecular weight was decreased by the addition of adipic acid.

We made our initial run to study the effect of adipic acid on the reaction of aspartic acid and succinic anhydride by adding 5% adipic acid to the 8:1 ratio material. Unexpectedly, there was a dramatic reduction in the extruder torque relative to just the 8:1 ratio of aspartic acid to succinic anhydride material in the absence of adipic acid, a larger effect than predicted for addition of a relatively small addition of adipic acid. Although Applicants do not wish to be bound to any particular theory they think that the added adipic acid could potentially fluidize the melt by two different mechanisms. First of all, the relatively low melting adipic acid (mp about 152° C.) could simply plasticize the reactant mixture. Secondly, the adipic acid could potentially incorporate into the polymer and make it more flexible and thus more fluid.

Extruder Synthesis of Aspartic Acid:Succinic Anhydride 10:1+5% Adipic Acid

A polymerization at 10:1 molar ratio of aspartic acid to succinic anhydride was run in the presence of 5% adipic acid at a temperature of 266° C. The FTIR spectrum of this material indicates that a good extent of reaction has occurred. The color of this material is roughly the same as that at the 8:1 ratio of aspartic acid: succinic anhydride material.

Extruder Synthesis of Aspartic Acid:Succinic Anhydride 20:1+5% Adipic Acid

We made up a mix with a 20:1 ratio of aspartic acid: succinic anhydride, with 5% adipic acid added. This material ran at a higher torque than the 10:1 ratio material. The color of this material is acceptable.

Titration Analysis

Representative samples were analyzed by titration in addition to the FTIR analysis. The table below shows the theoretical values and the experimental values for the selected samples. Only titration of hydrolyzed materials was done because at these ratios the materials are not soluble in 50% aqueous acetonitrile in unhydrolyzed form.

The values found in general are quite good (within roughly 2-9% of the anticipated values).

TABLE 9

| Sample | Titer, meq/g Hydrolyzed theoretical | Titer, meq/g Hydrolyzed experimental |
|---|---|---|
| 8:1, 243° C. | 11.4 | 10.9 |
| 8:1, 254° C. | 11.4 | 10.5 |
| 8:1 + 5% adipic, 266° C. | ~11.4 | 11.0 |
| 8:1 + 5% adipic, 266° C. | ~11.4 | 10.8 |
| 10:1 + 5% adipic, 266° C. | ~11.2 | 11.0 |
| 20:1 + 5% adipic, 266° C. | ~10.8 | 10.4 |

Molecular Weight Analysis

The effect on molecular weight of materials prepared at a ration of aspartic acid to succinic anhydride of 10:1 and 20:1 was determined. Further, the effect on molecular weight of the extrusion temperature of materials prepared at a ratio of aspartic acid to succinic anhydride of 8:1 at various extrusion temperatures was determined. Further, the effect on molecular weight of aspartic acid and succinic anhydride materials prepared in the presence of 5% adipic acid was determined. The results obtained are shown in the following table.

TABLE 10

| Sample Composition | Extruder Temp. (° C.) | Molecular Weight ($m_p$) (Dalton) |
|---|---|---|
| 8:1 aspartic acid:succinic anhydride | 243 | 1000 |
| 8:1 aspartic acid:succinic anhydride | 254 | 1000 |
| 8:1 aspartic acid:succinic anhydride | 266 | 1100 |
| 8:1 aspartic acid:succinic anhydride + 5% adipic acid | 266 | 810 |
| 10:1 aspartic acid:succinic anhydride + 5% adipic acid | 266 | 970 |
| 20:1 aspartic acid:succinic anhydride + 5% adipic acid | 266 | 2300 |

The invention claimed:

1. A method of producing a copolymer of D-sorbitol comprising polymerizing said D-sorbitol with a comonomer in the absence of a solvent.

2. The method of claim 1, wherein said comonomer is citric acid.

3. The method of claim 1, wherein said comonomer is a salt of citric acid.

4. The method of claim 3, wherein said salt of citric acid is selected from the group consisting of a fully neutralized citrate, a citrate salt containing two free carboxyl hydrogens and a citrate salt containing one free carboxyl hydrogen.

5. The method of claim 3, wherein said salt contains a cation selected from the group consisting of a cation of the Group Ia, IIa, IIIa, IVa, Va, VIa, VIIa, VIIIa, Ib, IIb, and IIIb of the periodic table of elements.

6. The method of claim 2, wherein said citric acid and said D-sorbitol are present at a molar ration of from 1:1 to 10:1.

7. The method of claim 2, further comprising a starch.

8. The method of claim 1, wherein said comonomer is L-aspartic acid.

9. The method of claim 8, wherein said L-aspartic acid and said D-sorbitol are present at a molar ration of from 1:1 to 10:1.

10. The method of claim 1, wherein said polymerizing is carried out in the presence of a catalyst.

11. The method of claim 10, wherein said catalyst is selected from the group consisting of an acid and a base.

12. The method of claim 8, further comprising a starch.

13. The method of claim 8, wherein said copolymer formed contains gel.

14. The method of claim 2, wherein said polymerizing is carried out at a temperature of from 100° C. to 200° C.

15. The method of claim 8, further comprising succinic anhydride.

16. The method of claim 15, wherein said L-aspartic acid and said D-sorbitol are present at a molar ratio of from 1:1 to 1:6.

17. The method of claim 15, wherein said succinic anhydride is present in a range of from 1 to 15 wt % based on the combined amounts of L-aspartic acid and D-sorbitol.

18. The method of claim 15, wherein said polymerizing takes place in an oven, an extruder or a mixer.

19. The copolymer formed by the method of claim 1.

20. The copolymer formed by the method of claim 2.

21. The copolymer formed by the method of claim 3.

22. The copolymer formed by the method of claim 7.

23. The copolymer formed by the method of claim 8.

24. The copolymer formed by the method of claim 12.

25. The copolymer formed by the method of claim 15.

26. A method of producing a copolymer, comprising polymerizing succinic anhydride, L-aspartic acid and adipic acid.

27. The method of claim 26, wherein said polymerizing is carried out in the absence of a solvent.

28. The method of claim 26, wherein said succinic anhydride and said L-aspartic acid are present in a ratio of from 1:1 to 1:30, including all increments within this range.

29. The method of claim 26, wherein said adipic acid is present in an amount of from 1 to 5 wt %, based on the combined amount of the succinic anhydride and L-aspartic acid.

30. The copolymer formed by the method of claim 26.

31. The method of claim 1, further comprising a polymer additive.

32. The method of claim 26, further comprising a polymer additive.

33. The method of claim 1, wherein said comonomer is comprised of aspartic acid, starch and citric acid.

* * * * *

UNITED STATES PATENT AND TRADEMARK OFFICE
CERTIFICATE OF CORRECTION

PATENT NO. : 7,256,251 B2
APPLICATION NO. : 11/059678
DATED : August 14, 2007
INVENTOR(S) : Swift et al.

Page 1 of 1

It is certified that error appears in the above-identified patent and that said Letters Patent is hereby corrected as shown below:

Columns 5-6, in Scheme 1, the formula under the arrow "·$H_2O$" should be: -- -$H_2O$--;

Columns 7-8, in Scheme 1, the formula under the arrow pointed to possible linear product "·$H_2O$" should be: -- -$H_2O$--;

Column 8, last line "Group Ia" should be: --Group IIa--;

Column 9, line 44, "rea" should be: --reaction--;

Column 14, line 15 "sorbitoucitric acid" should be: --sorbitol/citric acid--;

Column 18, line 61 "[hydroxylmethylamino]" should be: --[hydroxyl methylamino]--.

Signed and Sealed this

Thirtieth Day of October, 2007

JON W. DUDAS
*Director of the United States Patent and Trademark Office*